(12) United States Patent
Kobuke et al.

(10) Patent No.: US 7,767,808 B2
(45) Date of Patent: Aug. 3, 2010

(54) PORPHYRIN-PHTHALOCYANINE DIMER AND TETRAMER HAVING DIRECTLY-BOUND π ELECTRON SYSTEMS AND PRODUCTION METHOD THEREOF

(75) Inventors: Yoshiaki Kobuke, Ikoma (JP); Akiharu Satake, Ikoma (JP); Kazuya Ogawa, Ikoma (JP)

(73) Assignee: National University Corporation Nara Institute of Science and Technology, Ikoma-shi (JP)

( * ) Notice: Subject to any disclaimer, the term of this patent is extended or adjusted under 35 U.S.C. 154(b) by 1013 days.

(21) Appl. No.: 11/442,567

(22) Filed: May 30, 2006

(65) Prior Publication Data

US 2006/0217538 A1    Sep. 28, 2006

Related U.S. Application Data

(63) Continuation of application No. PCT/JP2004/017865, filed on Dec. 1, 2004.

(30) Foreign Application Priority Data

Dec. 1, 2003    (JP)    ............................. 2003-402169

(51) Int. Cl.
   *C07B 47/00*    (2006.01)
(52) U.S. Cl. .................................... 540/145
(58) Field of Classification Search .................. 540/145

See application file for complete search history.

(56) References Cited

U.S. PATENT DOCUMENTS

| | | | |
|---|---|---|---|
| 6,429,310 B2 | 8/2002 | Kobuke et al. |
| 6,602,998 B2 | 8/2003 | Kobuke et al. |
| 6,727,358 B2 | 4/2004 | Kobuke et al. |
| 7,022,840 B2 | 4/2006 | Kobuke et al. |
| 2004/0072988 A1 | 4/2004 | Kobuke et al. |
| 2004/0202876 A1 | 10/2004 | Kobuke et al. |

FOREIGN PATENT DOCUMENTS

| | | |
|---|---|---|
| JP | 2001-213883 | 8/2001 |
| JP | 2001-253883 | 9/2001 |
| JP | 2003-103932 | 4/2003 |
| JP | 2003-123863 | 4/2003 |
| JP | 2003-231688 | 8/2003 |

OTHER PUBLICATIONS

Kazuya Kameyama et al, "Light-harvesting composites . . . ", Tetrahedron Letters 45 (2004) 7617-7620.*

Hong-Jian Tian, "Singlet-singlet intramolecular energy and electron transfer in covalently-linked porphyrin-phthalocyanine heterodimers", *J. Photochem. Photobiol. A: Chem.*, 72, 1993, pp. 163-168.

Hong-Jian Tian et al, "Solvent effects on competitive intramolecular electron transfer and energy transfer in a covalently linked porphyrin-phthalocyanine heterodimer", *Chinese Journal of Chemistry*, vol. 14, No. 5, 1996, pp. 412-420.

Xi-You Li et al, "Synthesis and photophysical properties of porphyrin-phthalocyanine heterodimer linked by piperazine", *Chinese Journal of Chemistry*, vol. 16, No. 2, 1998, pp. 97-108.

Li Li et al, "Photoinduced Electron Transfer and Charge Separation in Anthraquinone-substituted Porphyrin-Phthalocyanine Heterodimer", *J. Chem. Soc., Chem. Commun.*, 1991, pp. 619-620.

Serge Gaspard et al, "The First Synthesis of Covalently Linked Mixed Dimer Complexes containing Phthalocyanine and Porphyrin", *J. Chem. Soc., Chem. Commun.*, 1986, pp. 1239-1240.

Jonathan M. Sutton et al, "First synthesis of porphyrin-phthalocyanine heterodimers with a direct ethynyl linkage", *Chem. Commun.*, 2001, pp. 2014-2015.

Junzhong Li et al, "Synthesis and Properties of Star-Shaped Multiporphyrin-Phthalocyanine Light-Harvesting Arrays", *J. Org. Chem.*, 64, 1999, pp. 9090-9100.

Sung Ik Yang et al, "Synthesis and excited-stated photodynamics of phenylethyne-linked porphyrin-phthalocyanine dyads", *J. Mater. Chem.*, 10, 2000, pp. 283-296.

Kazuya Ogawa et al, "Formation of a Giant Supramolecular Porphyrin Array by Self-Coordination", *Angew. Chem. Int. Ed.*, 39, No. 22, 2000, pp. 4070-4073.

Akihiro Nomoto et al, "Photocurrent generation system incorporated with antenna function", *Chem. Commun.*, 2002, pp. 1104-1105.

Akihiro Nomoto et al, "Porphyrin hetero-dimer as charge separating system for photocurrent generation", *Chem. Commun.*, 2003, pp. 1074-1075.

Kazuya Ogawa et al, "Large Third-Order Optical Nonlinearity of Self-Assembled Porphyrin Oligomers", *J. Am. Chem. Soc.*, vol. 124, No. 1, 2002, pp. 22-23.

* cited by examiner

*Primary Examiner*—James O. Wilson
*Assistant Examiner*—Paul V. Ward
(74) *Attorney, Agent, or Firm*—Oblon, Spivak, McClelland, Maier & Neustadt, L.L.P.

(57) ABSTRACT

A porphyrin/phthalocyanine dimer represented by the following Formula (A-1) and a tetramer represented by the following Formula (A-2) (where $R_1$, $R_2$ and $R_3$ may be the same or different, and each represents a hydrogen atom or an alkyl or alkyloxy group; $M_1$ and $M_2$ may be the same or different, and each represents two protons or a bivalent or trivalent metal ion; $X_1$ represents a single bond or an alkylene group; X represents —O—, —S—, >$NR_{101}$ (where $R_{101}$ represents H or alkyl group), $CH_2$, or a single bond; Y represents 2H, =O or =S; m is an integer of 0 to 4; Z represents a five- or six-membered nitrogen-containing coordinating heteroaromatic ring group; provided that the multiple substituent groups represented by the same character may be the same or different.

[Formula 1]
(A-1)
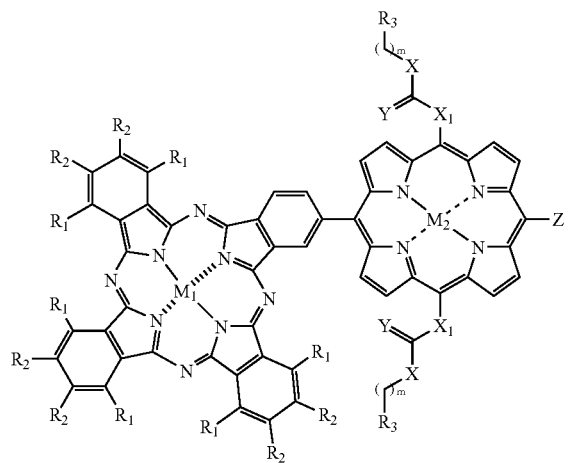
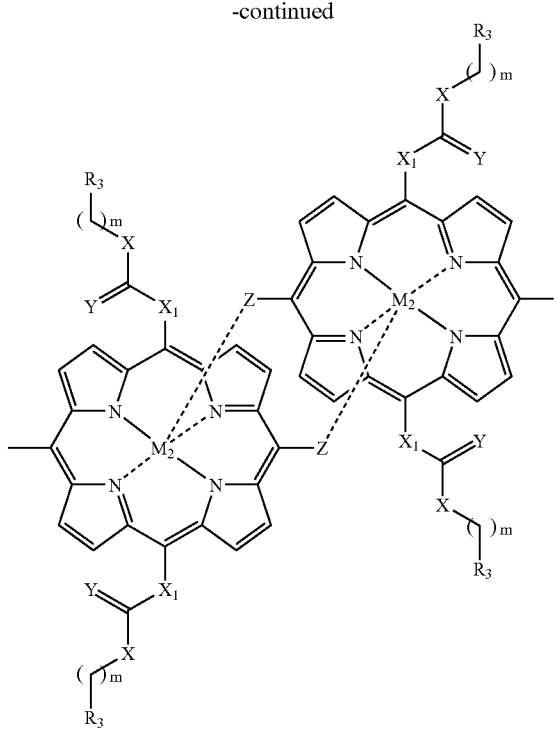
-continued
(A-2)
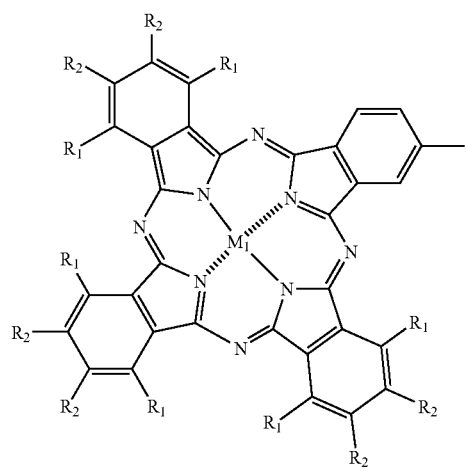
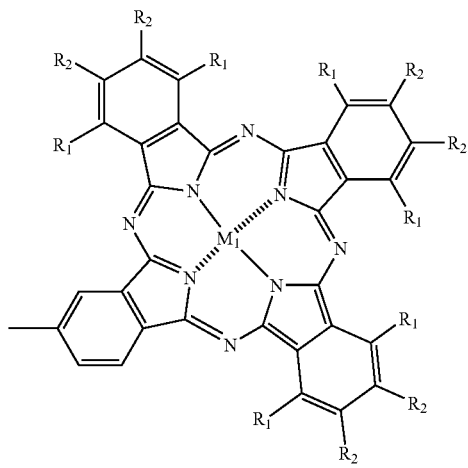
16 Claims, 4 Drawing Sheets

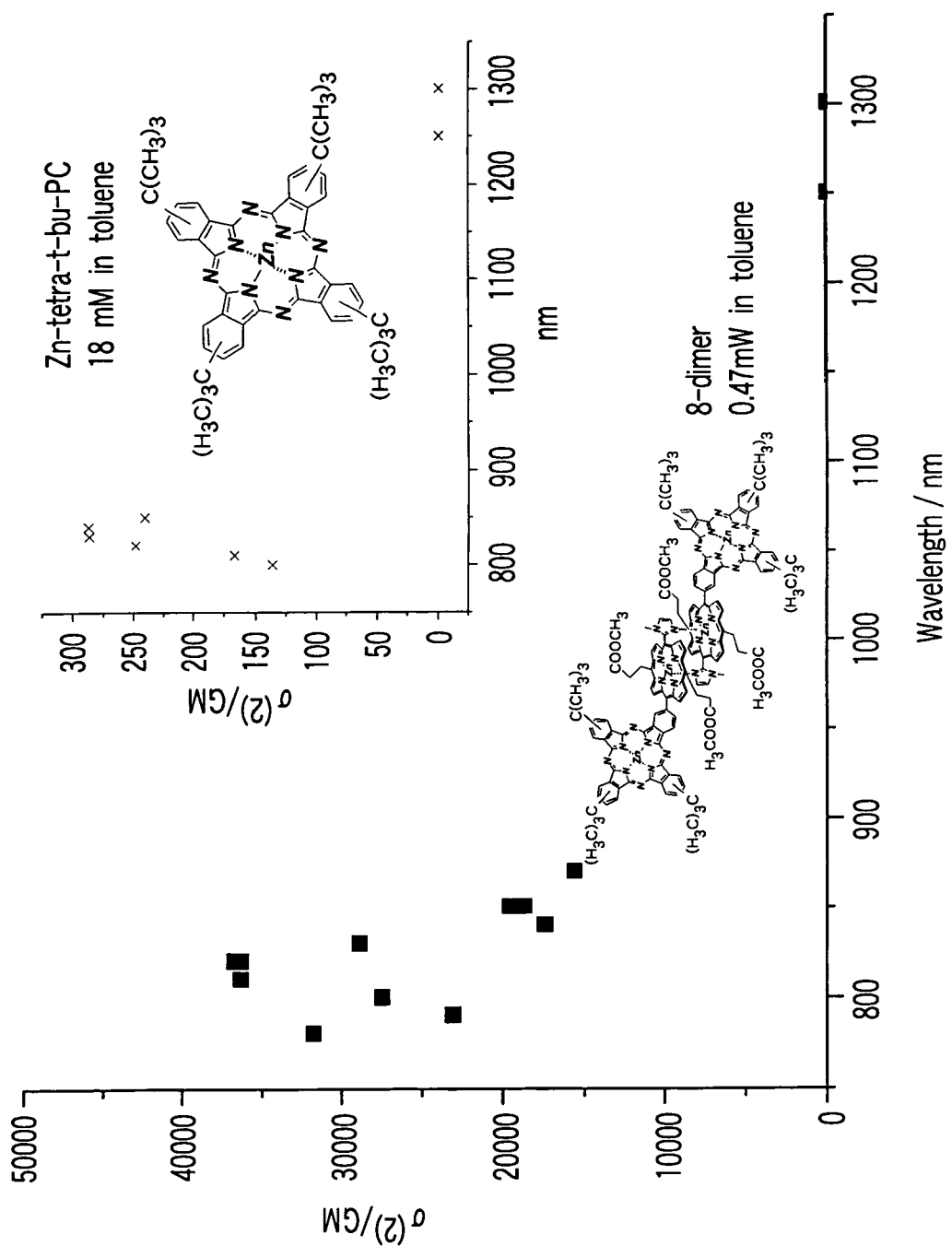
F I G. 5

PORPHYRIN-PHTHALOCYANINE DIMER AND TETRAMER HAVING DIRECTLY-BOUND π ELECTRON SYSTEMS AND PRODUCTION METHOD THEREOF

CROSS-REFERENCE TO RELATED APPLICATIONS

This is a Continuation Application of PCT Application No. PCT/JP2004/017865, filed Dec. 1, 2004, which was published under PCT Article 21(2) in Japanese.

This application is based upon and claims the benefit of priority from prior Japanese Patent Application No. 2003-402169, filed Dec. 1, 2003, the entire contents of which are incorporated herein by reference.

BACKGROUND OF THE INVENTION

1. Field of the Invention

The present invention relates to porphyrin-phthalocyanine dimer and tetramer having directly-bound π electron systems and a production method thereof.

2. Description of the Related Art

Porphyrins and phthalocyanines, which have a larger molar absorbance coefficient and are superior in photoelectronic properties, have been studied for application as various optical materials. Generally, phthalocyanines have an energy level lower than that of porphyrins, and thus theoretically, it would be possible that energy or electron transfer from porphyrin to phthalocyanine occurs if these compounds are connected to each other. Although there were reports on synthesis and optical properties of such dimers or multimers in which these compounds are connected to each other via one or more atoms, they were still unsatisfactory, in terms of the efficiency in energy or electron transfer (e.g., see the following Non-patent Documents 1 to 8). In addition, there is no report on use of the dimers and others described in these documents as functional terminal molecules, after various kinds of dimer molecules are introduced on the terminal thereof.

The present inventors have developed a method of introducing a variety of functional molecules on the terminal of a multimer having an imidazolyl group-containing porphyrin dimer as its constitutional unit (e.g., see the following Non-patent Document 9 and Patent Document 1). In addition, the present inventors have shown that it is possible to use a porphyrin compound having bisimidazolylporphyrin as its constitutional unit in photoelectric conversion elements (e.g., see the following Non-patent Document 10 and Patent Document 2) and three-dimensional nonlinear optical materials (e.g., see the following Non-patent Document 10 and Patent Document 3), by self-assembly of the compound.

Non-patent document 1: H. Tian, Q. Zhou, S. Shen, H. Xu, J. Photochem. Photobiol. A: Chem. 1993, 72, 163-168.

Non-patent document 2: H. Tian, Q. Zhou, S. Shen, H. Xu, Chin. J. Chem. 1996, 14, 412-420.

Non-patent document 3: X. Li, Q. Zhou, H. Tian, H. Xu, Chin. J. Chem. 1998, 16, 97-108.

Non-patent document 4: L. Li, S. Shen, Q. Yu, Q. Zhou, H. Xu, J. Chem. Soc. Chem. Commun. 1991, 619-620.

Non-patent document 5: S. Gaspard, C. Giannotti, P. Maillard, C. Schaeffer, T. Tran-Thi, J. Chem. Soc. Commun. 1986, 1239-1340.

Non-patent document 6: J. M. Sutton, R. W. Boyle, Chem. Commun. 2001, 2014-2015.

Non-patent document 7: J. Li, J. R. Diers, J. Seth, S. I. Yang, D. F. Bocian, D. Holten, J. S. Lindsey, J. Org. Chem. 1999, 64, 9090-9100.

Non-patent document 8: S. I. Yang, J. Li, H. S. Cho, D. Kim, D. F. Bocian, D. Holten, J. S. Lindsey, J. Mater. Chem. 2000, 10, 283-296.

Non-patent document 9: K. Ogawa and Y. Kobuke, Angew. Chem. Int. Ed. 2000, 39, 4070-4073.

Patent Document 1: Jpn. Pat. Appln. KOKAI Publication No. 2001-213883

Non-patent document 10: (a) A. Nomoto, Y. Kobuke, Chem. Commun. 2002, 1104-1105. (b) A. Nomoto, H. Mitsuoka, H. Ozeki, Y. Kobuke, Chem. Commun. 2003, 1074-1075.

Patent Document 2: Jpn. Pat. Appln. KOKAI Publication No. 2001-253883

Non-patent document 11: K. Ogawa, T. Zhang, K. Yoshihara, and Y. Kobuke, J. Am. Chem. Soc. 2002, 124, 22-23.

Patent Document 3: Jpn. Pat. Appln. KOKAI Publication No. 2003-231688

BRIEF SUMMARY OF THE INVENTION

An object of the present invention is to provide a molecule in which energy or electron transfer proceeds efficiently and a method for producing such a molecule.

As a result of intensive studies, the present inventors have accomplished the present invention based on the findings that high-efficiency energy and electron transfer from porphyrin to phthalocyanine occurs in a particular dimer of phthalocyanine and porphyrin; that it is possible to form a tetramer from the dimer by introducing a porphyrin-coordinating metal to the dimer and thus forming a complementary coordination bond between the coordinated metal and imidazole of another dimer, and high-efficiency energy and electron transfer also occurs in the tetramer; and that high-efficiency energy and electron transfer is also possible in a porphyrin multimer having the dimer residue as its molecular terminal group.

Specifically, the present invention provides the following dimer and tetramer.

(1) A porphyrin/phthalocyanine dimer represented by the following Formula (A-1):

[Formula 1]

(A-1)

where $R_1$, $R_2$ and $R_3$ may be the same or different, and each represents a hydrogen atom or an alkyl or alkyloxy group; $M_1$ and $M_2$ may be the same or different, and each represents two protons or a bivalent or trivalent metal ion; $X_1$ represents a single bond or an alkylene group; X represents —O—, —S—, $>NR_{101}$ (where $R_{101}$ represents H or alkyl group), $CH_2$, or a single bond; Y represents 2H, =O or =S; m is an integer of 0 to 4; Z represents a five- or six-membered nitrogen-containing coordinating heteroaromatic ring group; provided that the multiple substituent groups represented by the same character may be the same or different.

(2) A porphyrin/phthalocyanine tetramer, represented by the following Formula (A-2):

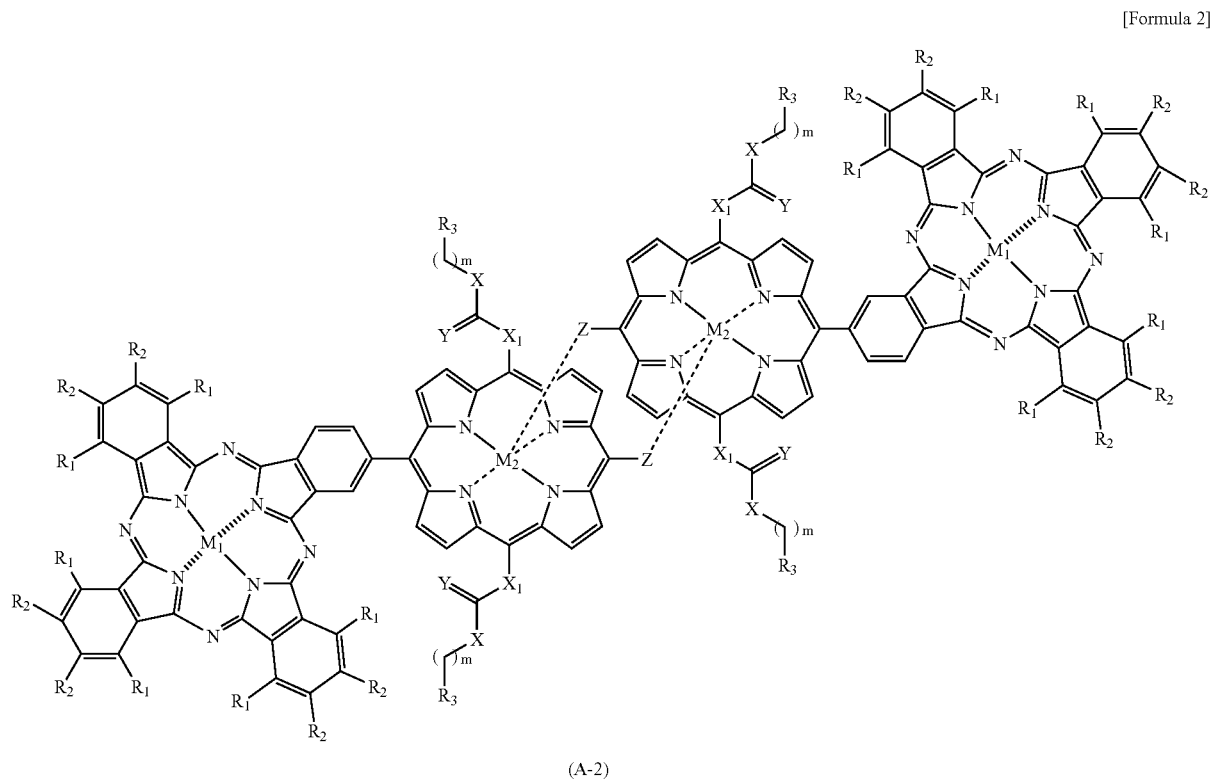

(A-2)

where $R_1$, $R_2$, $R_3$, $M_1$, $M_2$, $X_1$, X, Y, Z, and m are the same as those defined in the Formula (A-1) of (1); provided that $M_2$ is not two protons.

Further, the present invention provides a production method of the above-described dimer and tetramer.

(3) A method of producing the phthalocyanine/porphyrin dimer represented by the Formula (A-1) of (1):

(wherein respective substituent groups are the same as those defined in (1)), comprising reacting a phthalocyanine aldehyde represented by the following Formula (A-5):

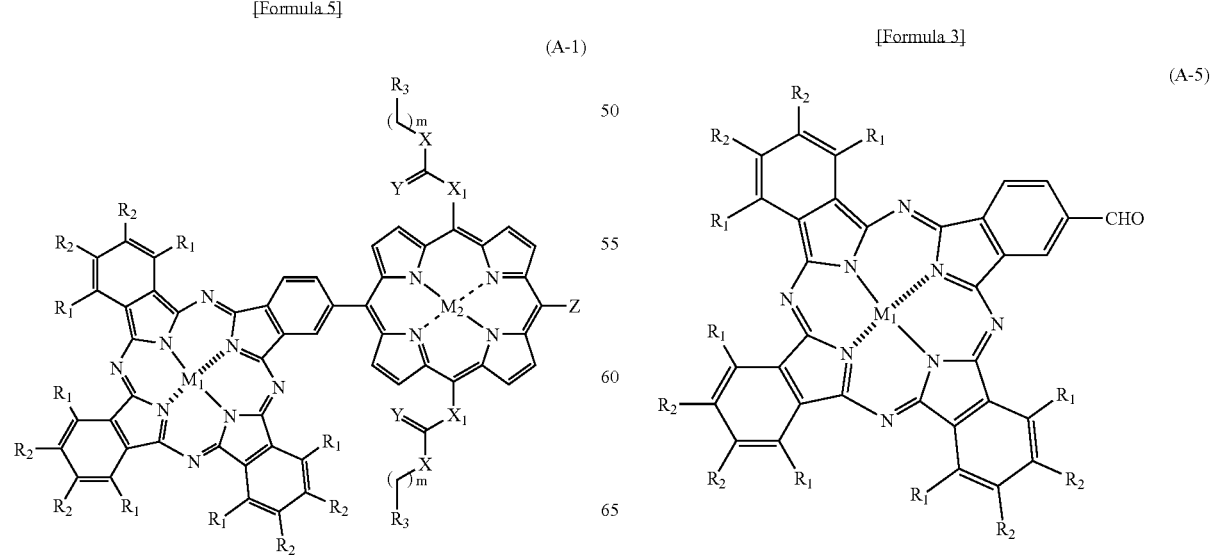

(where respective substituent groups are the same as those defined in the Formula (A-1) of (1)) with a dipyrrole compound represented by the following Formula (A-6):

[Formula 4]

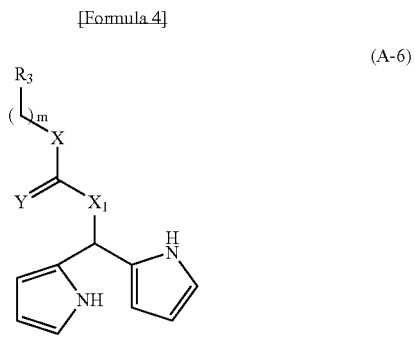

(A-6)

(where respective substituent groups are the same as those defined in the Formula (A-1) of (1)) in the presence of an organic solvent; then, reacting the product with an aldehyde represented by Z—CHO (Z is the same as that defined in the Formula (A-1) of (1)); and introducing $M_2$ as the porphyrin-ring central metal, when $M_2$ of the dimer is a metal ion and not two protons.

(4) A method of producing the porphyrin/phthalocyanine tetramer represented by the Formula (A-2) of (2), comprising self-assembling the phthalocyanine/porphyrin dimer represented by the Formula (A-1) of (1) (respective substituent groups are the same as those defined in the Formula (A-1) of (1); provided that $M_2$ is not two protons) in a nonpolar solvent.

BRIEF DESCRIPTION OF THE SEVERAL VIEWS OF THE DRAWING

FIG. 5 shows the two-photon absorption spectra of the dimer of the dimer 8 (ZnPc-ZnPor) of the present invention (porphyrin/phthalocyanine tetramer of the present invention) and a reference compound (Zn-tetra-t-bu-Pc).

DETAILED DESCRIPTION OF THE INVENTION

Figure 1:
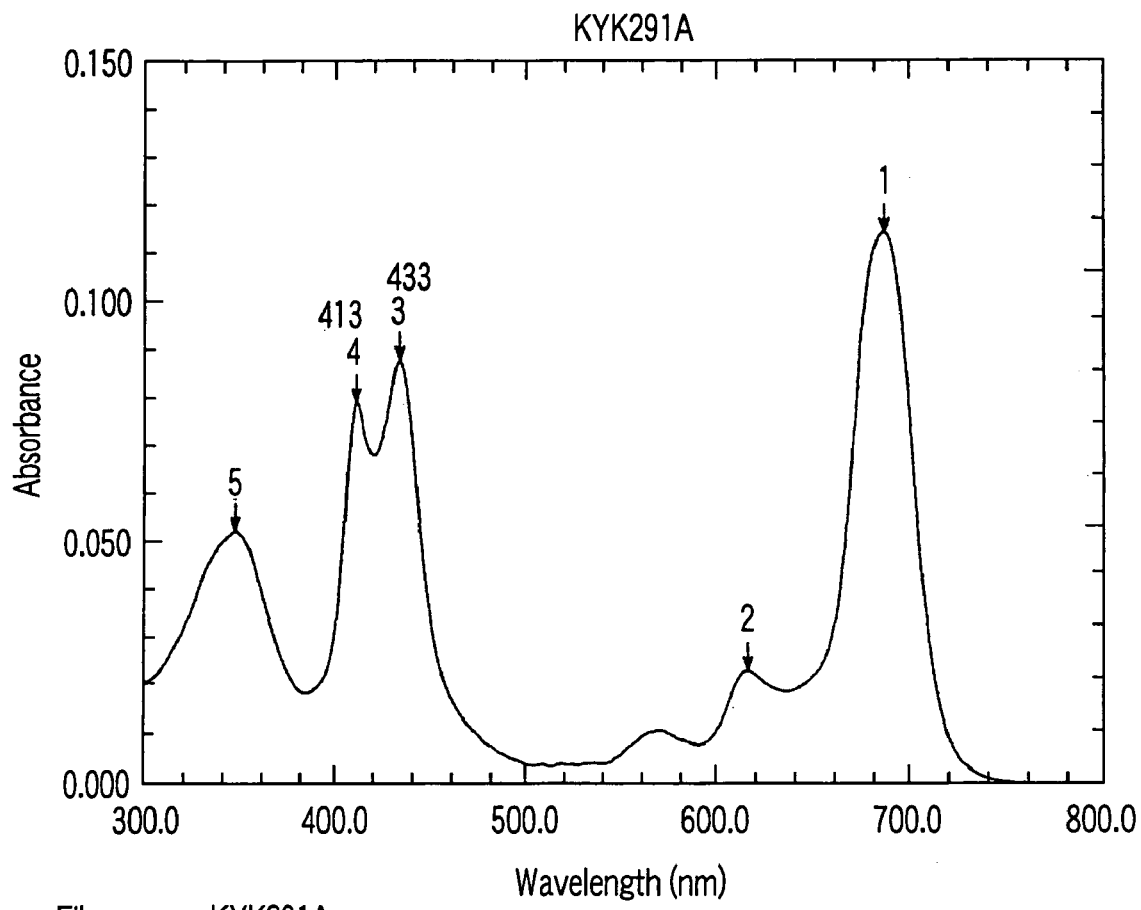
FIG. 1 shows the absorption spectrum of 8-dimer in chloroform.

The alkyl group in the present specification refers to a monovalent straight-chain, branched-chain or cyclic aliphatic group (hereinafter, the same shall apply to other groups having an alkyl group as the substituent group and alkyl-containing groups such as alkyloxy group).

In addition, each of the groups described below may have one or more substituents, as long as the compound of the present invention shows the advantageous effects according to the present invention.

(1) Porphyrin/Phthalocyanine Dimer Represented by Formula (A-1)

In the Formula (A-1), $R_1$, $R_2$ and $R_3$ may be the same or different, and each represents a hydrogen atom, an alkyl group, or an alkyloxy group. The carbon number of the alkyl group represented by $R_1$, $R_2$ and $R_3$ is not particularly limited, but generally, approximately 1 to 20 (preferably, 3 to 5). The alkyl or alkyloxy group represented by $R_1$, $R_2$ and $R_3$ is preferably a bulky group (e.g., tertiary alkyl group such as t-butyl), particularly for the purpose of prevention of π-π stacking between phthalocyanine molecules.

$M_1$ and $M_2$ may be the same or different, and each represents two protons or a bivalent or trivalent metal ion.

Examples of the bivalent or trivalent metal ions represented by $M_1$ and $M_2$ include metal ions that can be a central metal selected from typical metals and transition metals. The typical metals are metals in the groups 1A, 2A, 2B, 3B to 7B and 0 in the long-form periodic table, and specific examples thereof include Mg, Zn, Cd, Hg, Al, Ga, In, Tl, Si, Ge, Sn, Pb, P, As, Sb, Bi, and the like. The transition metals are metals in the groups 3A to 7A, 8 and 1B, and specific examples thereof include Sc, Y, lanthanoids (La, Ce, Pr, Nd, Pm, Sm, Eu, Gd, Tb, Dy, Ho, Er, Tm, Yb, and Lu), Ti, Zr, Hf, V, Nb, Ta, Cr, Mo, W, Mn, Tc, Re, Fe, Ru, Os, Co, Rh, Ir, Ni, Pd, Pt, Cu, Ag, Au, and the like.

$M_1$ and $M_2$ may be selected properly according to the intended purpose of the dimer of Formula (A-1) such as energy transfer or electron transfer. It is also possible to change the energy level and the oxidation-reduction potential of the dimer of Formula (A-1) by properly selecting the metal.

$X_1$ represents a single bond or an alkylene group. The carbon number of the alkylene group is not particularly limited, but generally, approximately 1 to 6 (preferably, 2 (because of easiness in preparing the raw material compound and expected functions of the product)).

X represents —O—, —S—, >$NR_{101}$ (where $R_{101}$ represents H or an alkyl group), $CH_2$, or a single bond.

The carbon number of the alkyl group represented by $R_{101}$ is not particularly limited, but preferably, approximately 1 to 4.

X is preferably —O—, in view of easiness in preparing the raw material compound and expected functions of the product.

Y represents =O, =S, or 2H. The case where Y represents 2H means that the two hydrogen atoms are bound to the carbon atom (to which Y is bound) by the single bond.

Y is preferably =O, in view of easiness in preparing the raw material compound and expected functions of the product.

m represents an integer of 0 to 4. m is preferably 1, in view of easiness in preparing the raw material compound and expected functions of the product.

In Formula (A-1), Z represents a five- or six-membered nitrogen-containing coordinating heteroaromatic ring group. The five- or six-membered nitrogen-containing coordinating heteroaromatic ring group is not particularly limited, as long as it is a five- or six-membered heterocycle having at least one nitrogen atom and has aromatic property. Heteroatoms other than nitrogen, e.g., oxygen, sulfur, and the like may be included. The nitrogen-containing coordinating heteroaromatic ring group may include its structure isomers, if present.

Examples of the five- and six-membered nitrogen-containing coordinating heteroaromatic ring groups include, but are not limited to, the following imidazolyl, oxazolyl, thiazolyl, and pyridyl groups.

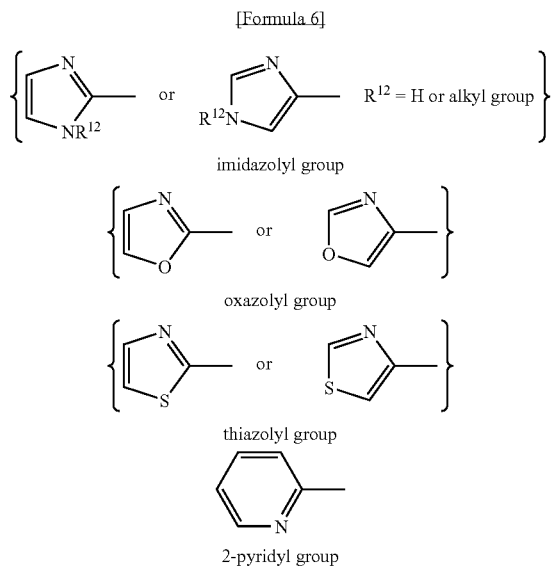

In the imidazolyl group, the alkyl group represented by $R^{12}$ is generally an alkyl group having 1 to 10 carbon atoms, preferably approximately 1 carbon atom, in view of easiness in preparing the raw material compound and expected functions of the product.

Z is preferably an imidazolyl group, in view of the strength of the bond between the porphyrin metal complex and the central metal.

The multiple same characters used in Formula (A-1) may be the same as or different from each other.

The definitions of the substituent groups in Formula (A-1) above are applied to those in Formula (A-2) and other formulae, unless otherwise specified.

In the dimer represented by Formula (A-1) described above, the π electron systems of porphyrin and phthalocyanine are conjugated directly, and thus the dimer allows high-efficiency energy and electron transfer from porphyrin to phthalocyanine (see Measurement Examples 2 to 4 described below).

In addition, it is possible to change the energy level and the oxidation-reduction potential of the molecule of the dimer represented by Formula (A-1) by properly selecting $M_1$ and $M_2$. For example, $M_1$ and $M_2$ are preferably $H_2$, Zn, Mg or the like, in terms of energy and electron transfer. Alternatively, $M_1$ and $M_2$ are preferably a trivalent metal such as Al (III) or Ga (III) due to possible improvement of polarizability, from the viewpoints of using it as a three-dimensional nonlinear material and the like. Particularly, $M_1$ and $M_2$ are preferably hydrogen, Zn, Mg, or the like, from the viewpoint of using it as a fluorescence probe, but $M_1$ and $M_2$ are not necessarily the same as each other. $M_2$ may be any one of the metals coordinating with imidazole such as Zn, Mg, Co, and Fe, in order to make the coordination structure of porphyrin. The metal may be so selected that the polarizability of the porphyrin and phthalocyanine can be controlled freely, when the compound is used as a nonlinear optical material. When a bivalent metal is used for porphyrin ($M_2$), use of higher valence of trivalent typical metal (e.g., Al (III), Ga (III), or the like) for phthalocyanine ($M_1$) is effective in improving the polarizability and giving greater advantageous effects.

It is also possible to control the ratio of energy transfer and electron transfer of the dimer of Formula (A-1), by changing the solvent for dissolving the dimer. For example, it is possible to increase the ratio of energy transfer, by using a solvent having a low-dielectric constant such as toluene. Alternatively, it is possible to increase the ratio of electron transfer, by using a solvent having a high-dielectric constant such as methylene chloride.

(2) Porphyrin/Phthalocyanine Tetramer Represented by Formula (A-2)

In the Formula (A-2), $R_1$, $R_2$, $R_3$, $M_1$, $M_2$, $X_1$, X, Y, Z and m are the same as those defined in Formula (A-1) above, and the favorable examples thereof are also the same as those defined in Formula (A-1). However, $M_2$ is not two protons.

In the tetramer represented by Formula (A-2) of the invention, a porphyrin-coordinating metal is introduced into the dimer represented by Formula (A-1) of the present invention, and the metal and Z (five- or six-membered nitrogen-containing coordinating heteroaromatic group) of another dimer form a complementary coordination bond.

Efficient energy transfer and electron transfer from porphyrin to phthalocyanine occurs in the tetramer represented by Formula (A-2) of the present invention. See the section of <Measurement Example 1> below.

Similarly to the dimer of Formula (A-1) above, it is also possible to control the ratio of energy and electron transfer of the tetramer represented by Formula (A-2) of the present invention, by changing a solvent for dissolving the tetramer.

(3) Method of Producing the Dimer Represented by Formula (A-1) of the Present Invention The dimer represented by Formula (A-1) can be prepared by reacting a phthalocyanine aldehyde represented by the following Formula (A-5):

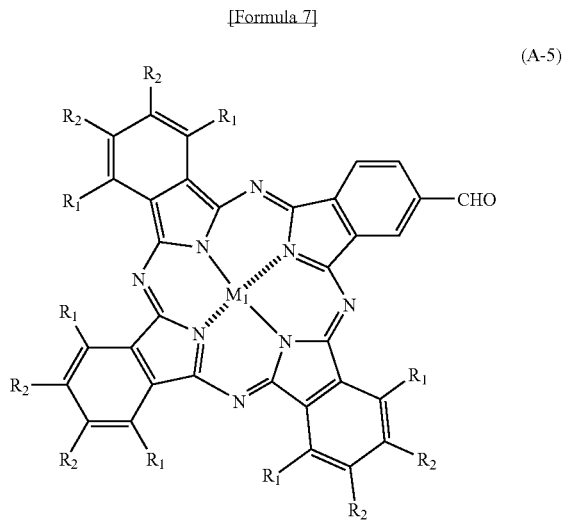

(where respective substituent groups are the same as those defined in Formula (A-1) of the section (1)) with a dipyrrole compound represented by the following Formula (A-6):

[Formula 8]

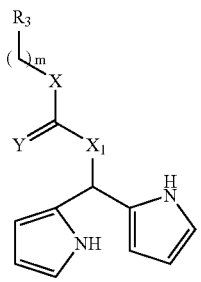

(A-6)

(where respective substituent groups are the same as those defined in Formula (A-1) of (1)) in the presence of an organic solvent; reacting the product with an aldehyde represented by Z—CHO (Z is the same as that defined in Formula (A-1) of (1)); and then introducing $M_2$ as the porphyrin-ring central metal, when the $M_2$ of the dimer is a metal ion and not two protons.

The phthalocyanine aldehyde represented by Formula (A-5) and the dipyrrole compound represented by Formula (A-6) can be prepared with reference to documents in the art.

Examples of the organic solvents for use in the reaction between the phthalocyanine aldehyde represented by Formula (A-5) and the dipyrrole compound represented by Formula (A-6) include chloroform, methylene chloride, and the like. The solvent can be used in an amount that the concentration of the phthalocyanine aldehyde of Formula (A-5) becomes approximately 1 to 2 mM.

The dipyrrole of Formula (A-6) can be used in an amount of 2 to 10 times larger in equivalence than the phthalocyanine aldehyde of Formula (A-5).

The reaction between these compounds is carried out generally under an inert atmosphere (e.g., argon or nitrogen) approximately for 5 hours under atmospheric pressure.

The reaction product obtained can be used in the next reaction with Z—CHO without purification.

The aldehyde Z—CHO may be purchased commercially or prepared with reference to documents in the art.

Examples of the organic solvents for use in the reaction between the reaction product and the aldehyde represented by Z—CHO include chloroform, methylene chloride, and the like. The solvent can be used in an amount such that the concentration of Z—CHO becomes approximately 1 to 2 mM.

Z—CHO can be used in an amount of 2 to 10 times larger in equivalence than the product obtained by the reaction between the aldehyde of Formula (A-5) and the dipyrrole of Formula (A-6).

The reaction between these compounds can be carried out generally under an inert atmosphere (e.g., argon, nitrogen) for approximately 5 hours under atmospheric pressure.

In preparation of the dimer of Formula (A-1) having a metal ion $M_2$ other than two protons, $M_2$ is introduced as the porphyrin-ring central metal into the dimer. The reaction of introducing the central metal $M_2$ is known in the art. For example, the reaction can be carried out by reacting the prior reaction product dissolved in a solvent such as chloroform with an acetate, hydrochloride, or other salt of metal $M_2$ dissolved in an organic solvent such as methanol. The amount of the metal salt added can be 5 to 20 times larger by mole than that of the dimer of Formula (A-1).

(4) Method of Preparing the Tetramer Represented by Formula (A-2) of the Present Invention The tetramer represented by Formula (A-2) of the present invention can be prepared by self-assembling the phthalocyanine/porphyrin dimer represented by Formula (A-1) of the present invention in a nonpolar solvent.

Examples of the nonpolar solvents for use include, but are not limited to, chloroform, benzene, toluene, and the like. The reaction conditions for self-assembling can be referred to Jpn. Pat. Appln. KOKAI Publication No. 2001-213883 (Patent Document 1), Jpn. Pat. Appln. KOKAI Publication No. 2001-213883 (Patent Document 2), and Jpn. Pat. Appln. KOKAI Publication No. 2003-231688 (Patent Document 3), which are described above as prior art documents. Briefly, a nonpolar solvent is used, normally, in an amount of 100 to 200 times larger by weight than the dimer compound, and the reaction solution is stirred at around room temperature for 1 to 3 hours, washed with an aqueous solvent such as water, removing the organic layer by evaporation, and thereby a crude product of the tetramer represented by Formula (A-2) can be prepared. The crude product obtained may be purified by size-exclusion chromatography (eluent: chloroform or other; column: JAI-GEL-2.5H, manufactured by Japan Analytical Industry Co., Ltd.).

EXAMPLES

Hereinafter, the present invention will be described with reference to Examples, but it should be understood that the present invention is not limited to these Examples.

Example 1

Preparation of $H_2Pc-H_2Por$ i) 4-Tert-butyldiiminoisoindoline 1

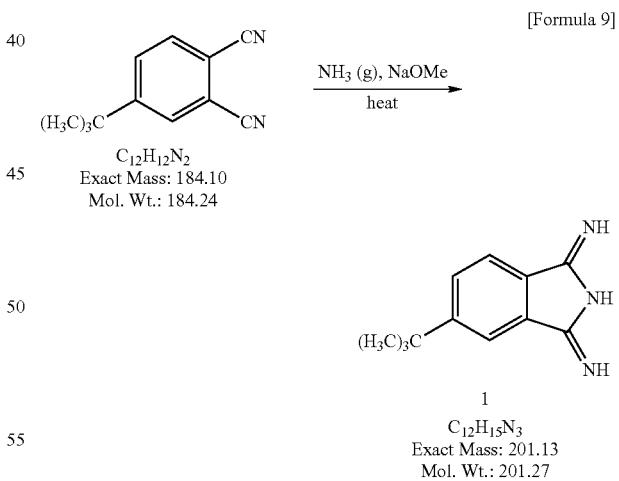

[Formula 9]

4-Tert-butylphthalonitrile (1.5 g, 8.14 mmol) was added to dry MeOH (300 mL) and the mixture was stirred until it was dissolved. After confirmation of complete dissolution, $NH_3$ gas was introduced for 15 minutes. NaOMe (34 mg, 0.63 mmol) suspended in 10 mL of dry MeOH was added to the reaction solution, and $NH_3$ gas was introduced repeatedly for 10 minutes at intervals of 20 minutes, while the reaction solution was refluxed under heating. Six hours after initiation of the reaction, disappearance of the raw materials was confirmed by TLC, and the reaction solution was cooled to room temperature and MeOH was evaporated. The residual pale-blue powdery compound was washed with cold water, to give a colorless solid. Yield: 1.34 g, 82%

Reference Document: Leznoff, Clifford C.; Greenberg, Shafrira; Tetrahedron Lett. 1989, 30, 5555-5558.

Leznoff, Clifford C.; Svirskaya, Polina I.; Khouw, Ben; Cerny, Ronald L.; J. Org. Chem. 1991, 56, 82-90.

ii) 4-Cyanodiiminoisoindoline 2

[Formula 10]

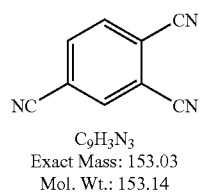

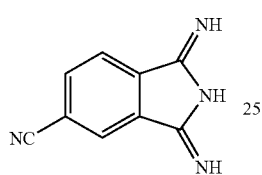

2
$C_9H_6N_4$
Exact Mass: 170.06
Mol. Wt.: 170.17

Tri-cyanobenzene 1.2 g (7.83 mmol) was dissolved in 200 mL of dry MeOH, and $NH_3$ gas was introduced for 15 minutes. NaOMe (34 mg, 0.63 mmol) suspended in 10 mL of dry MeOH was added to the reaction solution, and $NH_3$ gas was introduced repeatedly for 10 minutes at intervals of 20 minutes, while the reaction solution was refluxed under heating. Eight hours after initiation of the reaction, disappearance of the raw materials was confirmed by TLC, and the reaction solution was cooled to room temperature and MeOH was evaporated. The residual yellow powdery compound was washed with cold water, to give a pale-yellow solid.

Yield: 1.13 g, 85%

TLC: Rf=origin (methanol)

IR (KBr): ν=3436 nm (NH), 2230 nm (CN)

$^1$H NMR (DMSO-$d_6$, 270 MHz)

8.10-8.13 ppm [m, 1.1H (1H)]

8.22-8.25 ppm [m, 1.2H (1H)]

8.51 ppm [s, 1.0H (1H)] theoretical values in parenthesis (iii) Cyanophthalocyanine $3H_2$

[Formula 11]

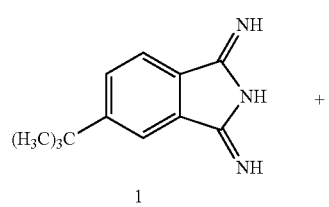

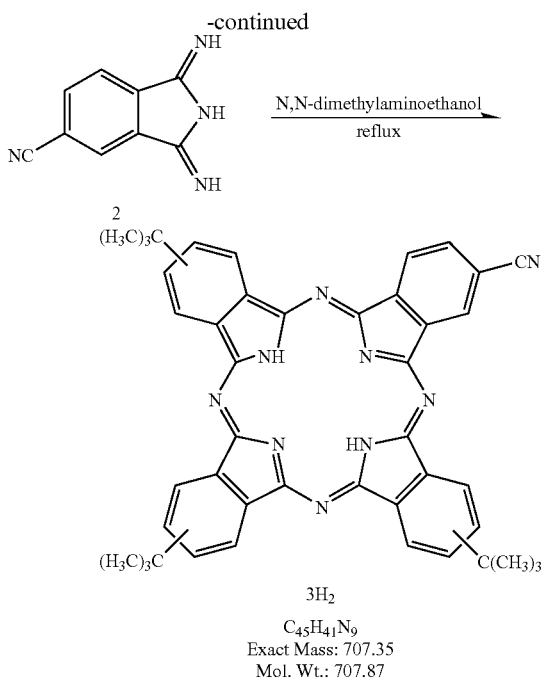

40 mg (0.24 mmol) of 4-cyanodiiminoisoindoline 2 and 180 mg (0.89 mmol) of 4-tert-butyldiiminoisoindoline 1 were dissolved in 50 mL of N,N-dimethylaminoethanol (DMAE) (hardly soluble), and the mixture was refluxed under heating. 12 hours after initiation of the reaction, disappearance of the two raw materials was confirmed by TLC, the solvent was evaporated by distillation under reduced pressure, the residue was dissolved in chloroform, and the mixture was washed with water. After evaporation of the solvent under reduced pressure, the residue was purified by silica gel chromatography [benzene:hexane=1:3 to benzene:$Et_3N$=10:1], to give a green compound $3H_2$.

Yield: 28 mg, 17%

TLC: Rf=0.5 (benzene:$Et_3N$=10:1)

UV-vis $\lambda_{max}$/nm (absorbance) $CHCl_3$: 695.5 nm (1.11), 666.5 nm (1.14), 639.0 nm (0.61), 341.5 nm (0.93)

IR (KBr): ν=2963 cm$^{-1}$, 2232 cm$^{-1}$ (CN), 1598 cm$^{-1}$

MALDI-TOFMASS (matrix: dithranol)

m/z: (M+H)$^+$ 708.7 (Calc. $C_{45}H_{42}N_9$: 707.35)

(iv) Formylphthalocyanine $4H_2$

[Formula 12]

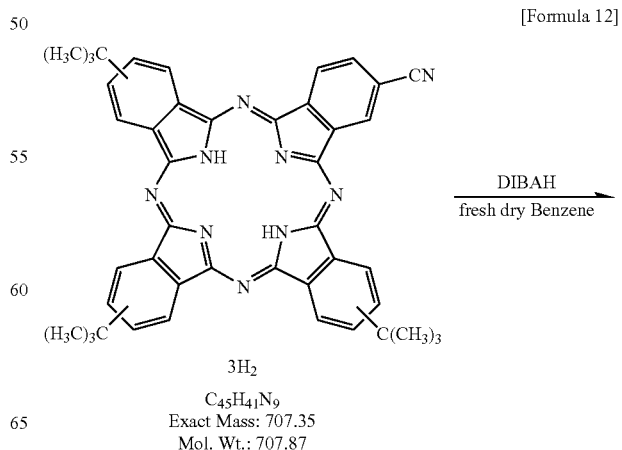

-continued

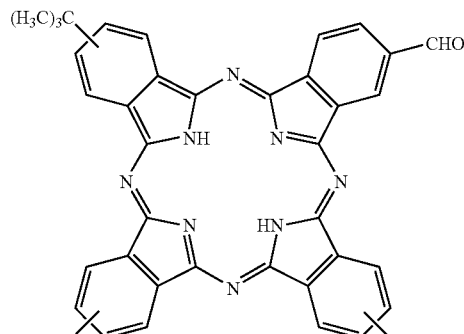

4H$_2$
C$_{45}$H$_{42}$N$_8$O
Exact Mass: 710.35
Mol. Wt.: 710.87

170 mg (0.24 mmol) of cyanophthalocyanine 3H$_2$ was dissolved in 30 mL of dry benzene at room temperature, and it was substituted with argon. 1.2 mL of DIBAH (1 M/hexane) (1.2×10$^{-3}$ mol) dissolved in 2 mL of benzene was added thereto. 6.0 hours after the addition, the disappearance of raw materials and the generation of a desired product by MALDI-TOF MASS were confirmed. After that, the reaction mixture was poured into aqueous 10% sulfuric acid solution, and then the organic layer was extracted with benzene. The organic layers were combined and dried over anhydrous sodium sulfate, and then, the solvent was evaporated. Purification by silica gel column chromatography (benzene:AcOEt=10:1) gave a desired aldehyde 4H$_2$.

Yield: 105 mg (62%)
TLC: Rf=0.7 benzene:AcOEt=10:1
UV-vis λ$_{max}$/nm (absorbance) CHCl$_3$: 691.0 nm (0.2143), 619.0 nm (0.0491), 345.0 nm (0.1018)
IR (KBr): ν=3418 cm$^{-1}$, 2923 cm$^{-1}$, 1693 cm$^{-1}$
MALDI-TOFMASS (matrix: dithranol)
m/z: M$^+$ 710.7 (Calc. C$_{45}$H$_{42}$N$_8$O: 710.35)

(v) Meso-(methoxycarbonylethyl)dipyrromethane (9)

The title compound was prepared by mixing methoxycarbonylpropanal (11.6 g, 0.1 mol) and pyrrole (280 mL, 4 mol) with stirring in the presence of trifluoroacetic acid (1.4 mL, 10 mmol), according to a method similar to that described in the document (Y. Tomohiro, A. Satake, Y. Kobuke, J. Org. Chem. 2001, 66, 8442-8446). The reaction product was purified by silica gel chromatography (hexane/EtOAc=5/1), to give meso-(methoxycarbonylethyl)dipyrromethane 9 (yield: 17 g (73%)).

$^1$H NMR (600 MHz, CDCl$_3$) δ: 2.22-2.26 (m, 2H), 2.29-2.33 (m, 2H), 3.63 (s, 3H), 3.99 (t, J=7.2 Hz, 1H), 6.05-6.07 (m, 2H, pyH4), 6.12-6.14 (m, 2H, pyH5), 6.58-6.62 (m, 2H, pyH2), 7.78 (br, 2H, NH);

$^{13}$C NMR (150 MHz, CDCl$_3$) δ 29.5, 31.9, 36.9, 51.6, 105.8, 108.1, 117.3, 132.4, 174.0.

(vi) 5(H$_2$Pc-H$_2$Por)

[Formula 13]

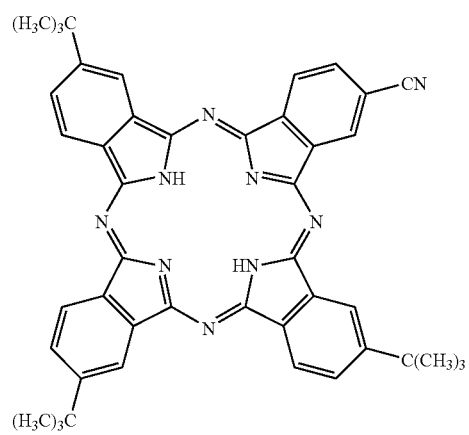

4H$_2$
C$_{45}$H$_{42}$N$_8$O
Exact Mass: 710.35
Mol. Wt.: 710.87

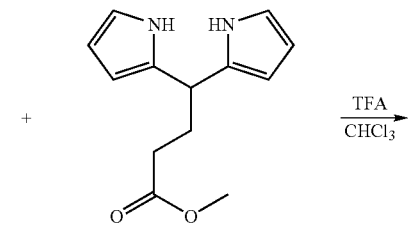

9
C$_{13}$H$_{16}$N$_2$O$_2$
Exact Mass: 232.12
Mol. Wt.: 232.28

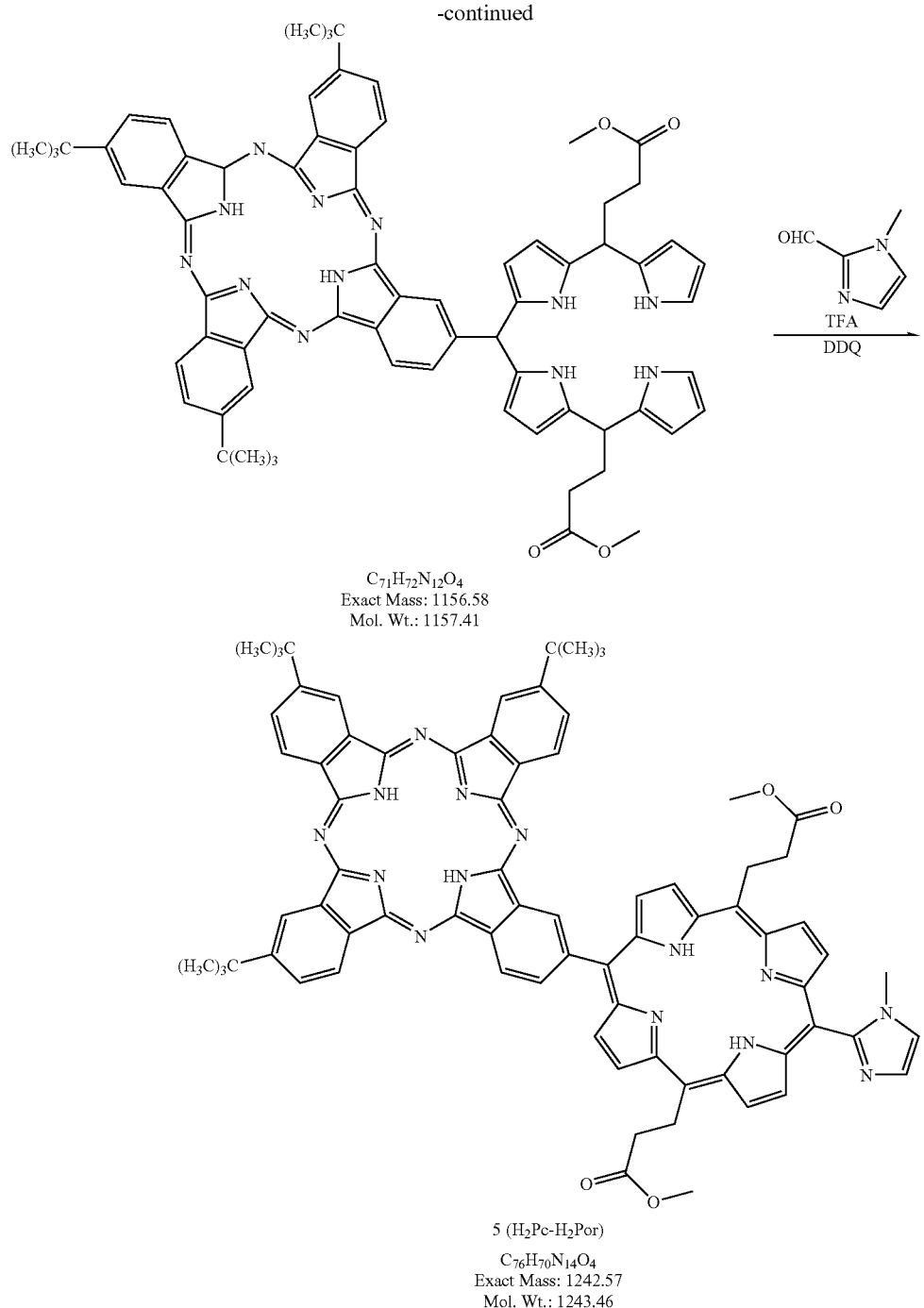

Formylphthalocyanine 4H$_2$ (36 mg, 0.05 mmol) and meso-(2-methoxycarbonylethyl)dipyrromethane 9 (117 mg, 0.5 mmol) were dissolved in argon-bubbled CHCl$_3$ (50 mL), TFA (9 μL, 0.125 mmol) was added thereto, and the mixture was stirred at room temperature for 8.5 hours. Then, imidazole aldehyde (50 mg, 0.45 mmol) was added thereto, and the mixture was stirred at room temperature. DDQ (170 mg, 0.75 mmol) was added after 12 hours, and the mixture was stirred at room temperature for 6 hours. The reaction solution was transferred into a separatory funnel and washed with aqueous saturated sodium bicarbonate solution, and then, insoluble matters in the organic layer were filtered with an extremely small amount of Celite. The organic layer was washed with aqueous saturated sodium bicarbonate solution and then with distilled water and dried over sodium sulfate, and the solvent was evaporated. The residue was purified by silica gel chromatography (CHCl$_3$:pyridine=10:1), to give a dark green compound 5 (H$_2$Pc-H$_2$Por) (5.3 mg, 9%).

TLC: Rf=0.5 CHCl$_3$:Py=10:1

UV-vis λ$_{max}$/nm (absorbance) CHCl$_3$: 697.00 nm (0.1085), 671.5 nm (0.1069), 645.50 nm (0.0481), 619.00 nm (0.0308), 517.50 nm (0.0134), 416.50 nm (0.2169), 345.00 nm (0.0742)

MALDI-TOFMASS (matrix: dithranol)
m/z: (M+H)$^+$ 1243.5 (Calc. $C_{76}H_{70}N_{14}O_4$: 1242.57)

Example 2

6($H_2$Pc-ZnPor)

2.4 mg (1.93 μmol) of 5 ($H_2$Pc-$H_2$Por) was dissolved in CHCl$_3$ (5 mL), three drops of saturated zinc acetate solution in MeOH was added, and the mixture was stirred at room temperature for 30 minutes. The reaction solution was washed with 30 mL of distilled water, the organic layer was dried over sodium sulfate, and the solvent was evaporated, to

[Formula 14]

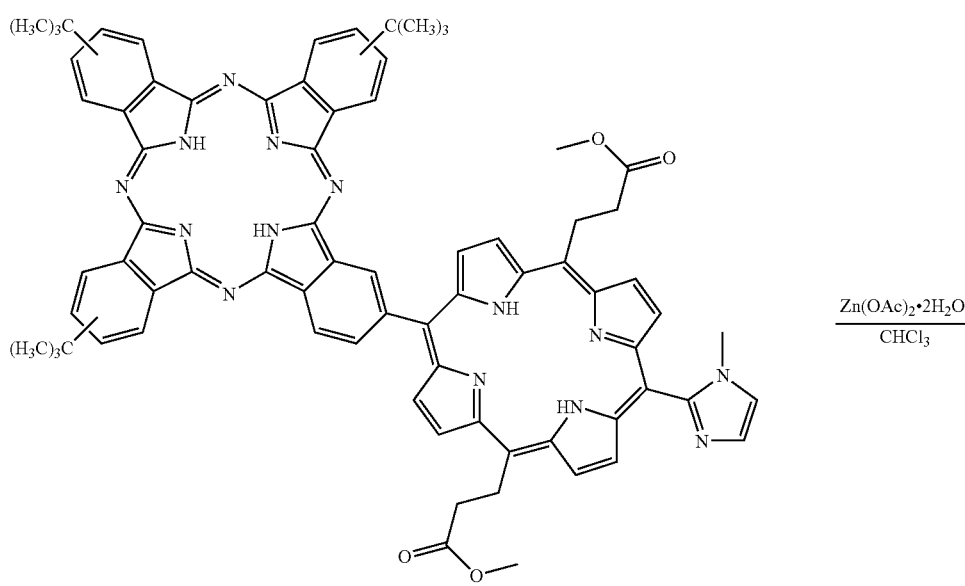

5 $H_2$Pc-$H_2$Por
$C_{76}H_{70}N_{14}O_4$
Exact Mass: 1242.57
Mol. Wt.: 1243.46

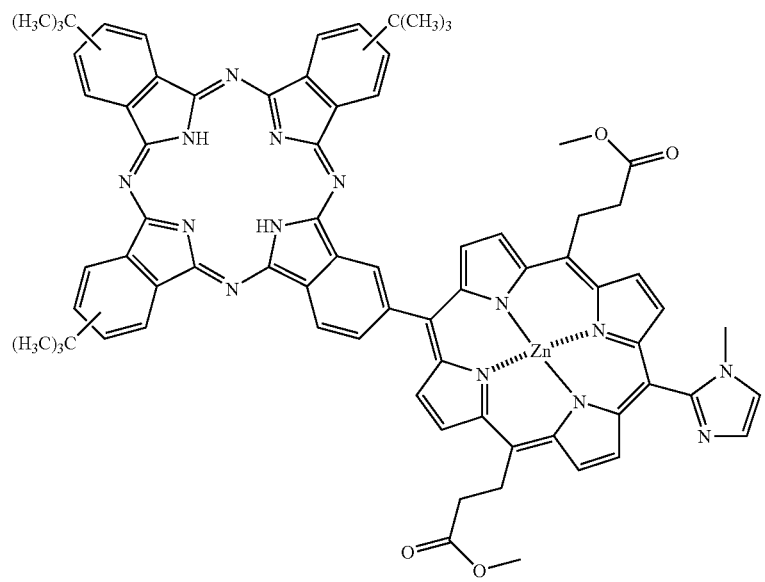

6 $H_2$Pc-ZnPor
$C_{76}H_{68}N_{14}O_4Zn$
Exact Mass: 1304.48
Mol. Wt.: 1306.84 give a green compound. A band of Rf=0.6 was isolated by silica gel column chromatography using CHCl$_3$:Py=10:1 as the eluent.

Yield: 2.1 mg, 83%

TLC: Rf=0.6 CHCl$_3$:Py=10:1

UV-vis $\lambda_{max}$/nm (absorbance) CHCl$_3$: 699.50 nm (0.0860), 675.50 nm (0.0733), 609.00 nm (0.0222), 571.00 nm (0.0122), 437.50 nm (0.0983), 413.00 nm (0.0888), 342.00 nm (0.0576)

MALDI-TOFMASS (matrix: dithranol)

m/z (M+H)$^+$ 1306.08 (Calc. C$_{76}$H$_{66}$N$_{14}$O$_4$Zn$_2$: 1304.48)

Example 3

ZnPc-H$_2$Por (i) 3Zn (ZnPc)

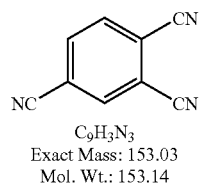

C$_9$H$_3$N$_3$
Exact Mass: 153.03
Mol. Wt.: 153.14

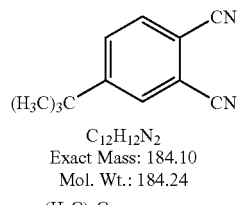

C$_{12}$H$_{12}$N$_2$
Exact Mass: 184.10
Mol. Wt.: 184.24

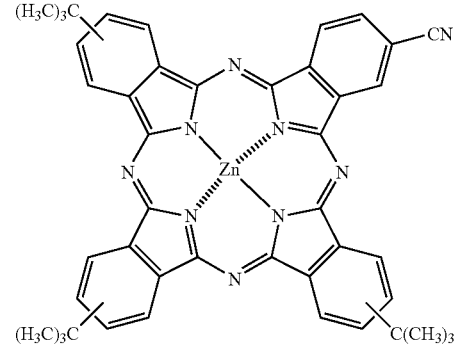

3Zn
C$_{45}$H$_{39}$N$_9$Zn
Exact Mass: 769.26
Mol. Wt.: 771.24

4-Cyanophthalonitrile (416 mg, 2.72 mmol), 4-tert-butylphthalonitrile (2.0 g, 11 mmol), and Zn(OAc)$_2$·2H$_2$O (4 g, 18.15 mmol) were ground in a mortar, and the resulting mixture was placed in a round-bottomed flask and heated in a salt bath at 230° C. Heating was stopped when the gas generation subsided after 60 minutes. The mixture was cooled to room temperature, washed with MeOH and water in that order, and dried under reduced pressure. The blue compound obtained was purified by silica gel column chromatography (benzene to benzene:ethyl acetate=7:1), to give purified 3Zn (594 mg, 28%).

TLC: Rf=0.7, benzene:AcOEt=7:1

UV-vis $\lambda_{max}$/nm (absorbance) CHCl$_3$: 692.0 nm (0.44), 669.0 nm (0.37), 636.0 nm (0.14), 342.0 nm (0.30)

IR(KBr): ν: 2958 cm$^{-1}$, 2224 cm$^{-1}$ (CN)

$^1$H NMR (DMSO-d$_6$, 270 MHz):

1.31-1.41 ppm [m, 26.1H (27H), tert-butyl]

7.68-7.69 ppm [m, 3.2H (3H), H$_2$]

7.92 ppm [m, 2.0H (2H), (H$_4$, H$_6$)]

8.06-8-12 ppm [m, 6.0H(6H), (H$_1$, H$_3$)]

9.11 ppm [m, 1.2H (1H), H$_5$] theoretical values in parenthesis

MALDI-TOFMASS (matrix: dithranol)

m/z: M$^+$ 769.49 (Calc. C$_{45}$H$_{39}$N$_9$Zn: 769.26)

(ii) 4Zn

[Formula 16]

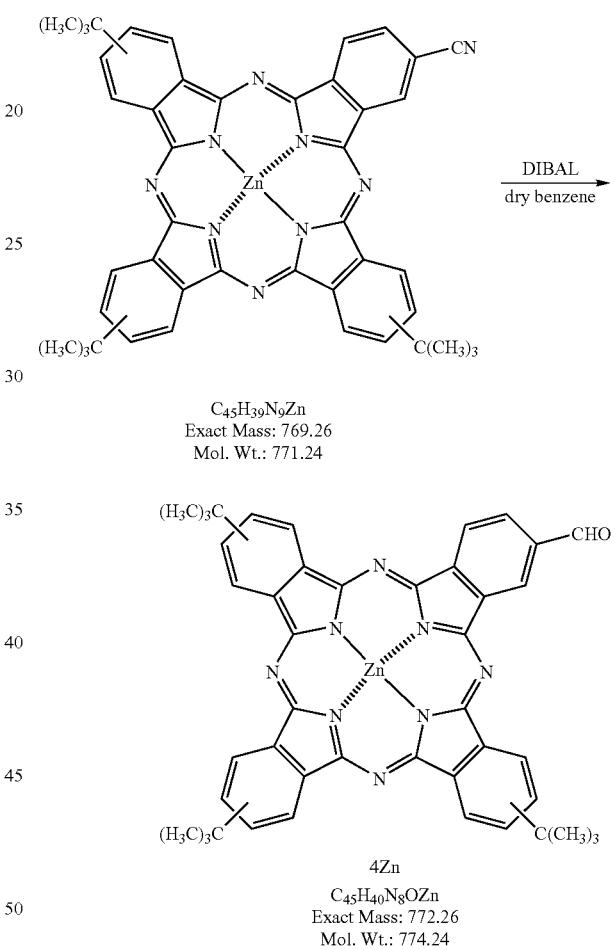

3(ZnPc) 141 mg/0.183 mmol

DIBAL (1 M hexane solution) 3 eq.

Dry benzene 13 mL+2 mL

Preparative Method

3Zn was dissolved in dry benzene (13 mL) at room temperature, it was substituted with argon, and 0.55 mL (0.55 mmol) of DIBAH (1 M/hexane) dissolved in 2 mL of benzene was added gradually thereto. After dropwise addition, the mixture was stirred for 5 hours, the reaction solution was washed with 10% dilute sulfuric acid, and the benzene layer was separated. Then, the aqueous layer was extracted with CHCl$_3$, and the organic layers were combined, concentrated and dried, to give a blue compound. A band of Rf=0.6 was isolated by silica gel column chromatography using benzene:AcOEt=5:1 as the eluent.
Yield: 108 mg, 76%
TLC: Rf=0.6, benzene:AcOEt=5:1
UV-vis $\lambda_{max}$/nm (absorbance) CHCl$_3$: 693.5 nm (0.2612), 674.0 nm (0.2586), 614.5 nm (0.0577), 352.5 nm (0.1599)
IR(KBr): ν: 2958 cm$^{-1}$, 1643 cm$^{-1}$ (C=O)
MALDI-TOFMASS (matrix: dithranol)
m/z: M$^+$ 769.49 (Calc. C$_{45}$H$_{39}$N$_9$Zn: 769.26)
(iii) 7 (ZnPc-H$_2$Por)
[Formula 17]
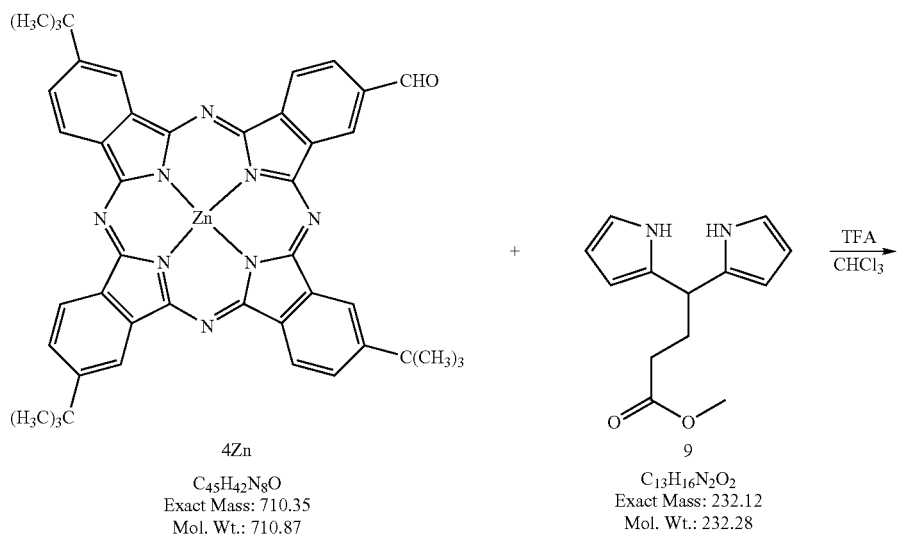
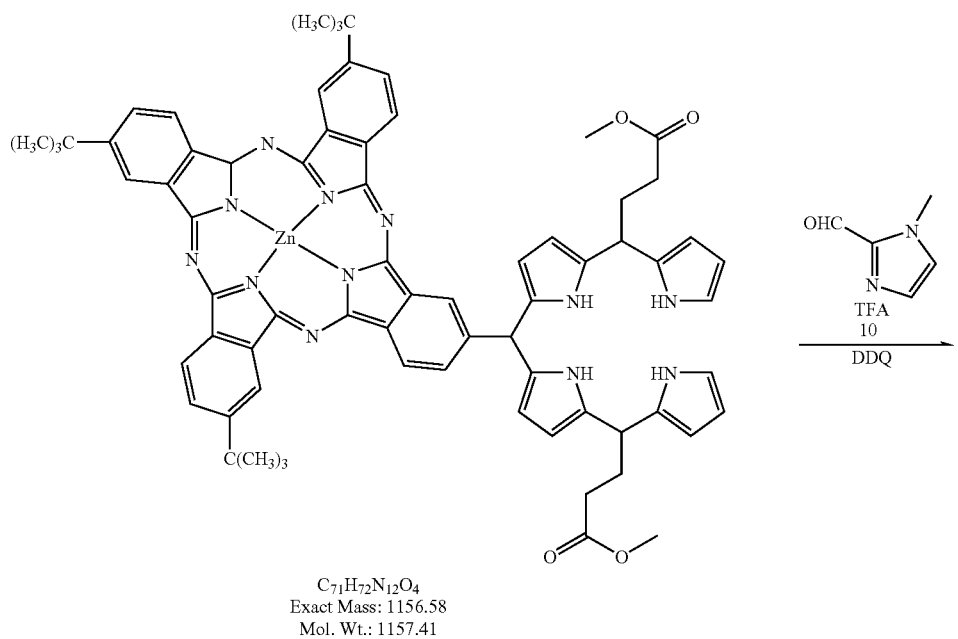

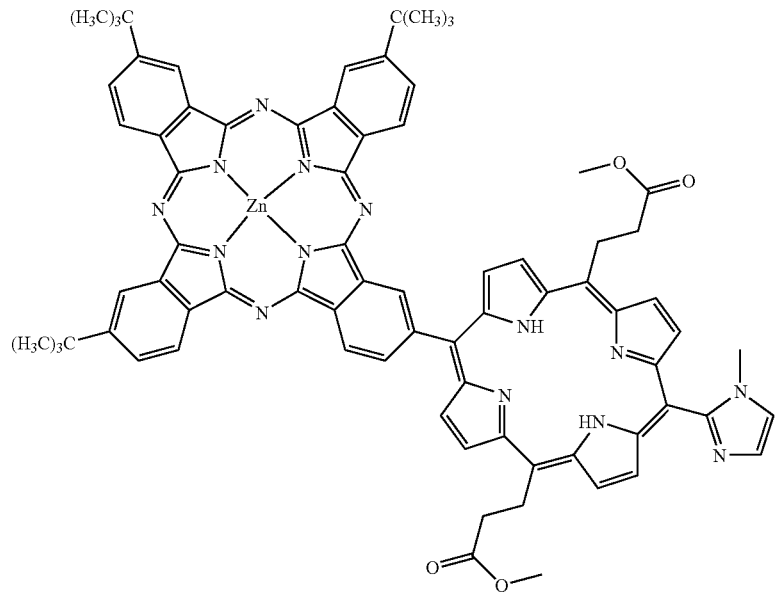

7 (H₂Pc-H₂Por)
C₇₆H₇₀N₁₄O₄
Exact Mass: 1242.57
Mol. Wt.: 1243.46

4Zn (15 mg, 0.019 mmol) and meso-(2-methoxycarbonyl-ethyl)dipyrromethane 9 (26 mg, 0.057 mmol) were dissolved in argon-bubbled CHCl₃ (10 mL), and TFA (4.2 μL, 0.057 mmol) was added thereto while the solution was stirred at room temperature. After 4.5 hours, a solution of Im-CHO 10 (10.5 mg, 0.095 mmol) and TFA (10 μL, 0.133 mmol) dissolved in CHCl₃ (2.0 mL) was added thereto, and the mixture was further stirred. After 1.5 hours, DDQ (38 mg, 0.171 mmol) was added, and the mixture was stirred for 4 hours. The reaction solution was poured into aqueous saturated sodium bicarbonate solution, and washed with distilled water in a separating funnel. The organic layer was dried over sodium sulfate, the solvent was evaporated, and the residue was purified by silica gel column chromatography (Py:CHCl₃=15:1), to give 7 (ZnPc-H₂Por) of RF=0.5, as a bright green solid.

Yield: 3.1 mg, 13%
TLC: Rf=0.5, Py:CHCl₃=15:1

UV-vis $\lambda_{max}$/nm (absorbance) CHCl₃: 693.00 nm (0.2648), 623.50 nm (0.0575), 519.00 nm (0.0233), 422.50 nm (0.2823), 352.00 nm (0.1716)

MALDI-TOFMASS (matrix: dithranol)
m/z: (M+H)⁺ 1305.49 (Calc. C₇₆H₆₈N₁₄O₄Zn: 1304.48)

[Formula 18]

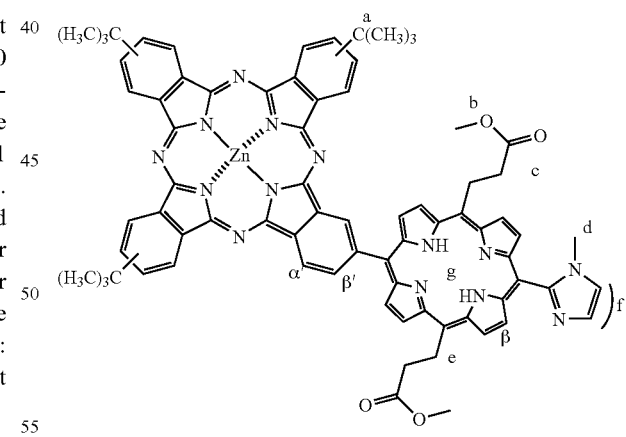

¹H NMR (Pyridine-d₅, 600 MHz)
−2.9–−2.3 ppm [g 0.96 H (2H), Por-inner H]
1.2-1.5 ppm [a 28.0 H (27H), tert-butyl]
2.7-3.7 ppm [b, c, d, 13.0 H (13H), OMe-, CH₂—, Imi-Me]
5.1-5.7 ppm [e, 4.0 H (4H), Por-CH₂—]
7.3-8.3 ppm [f, α', β', 9.0 H (9H), Imi, Pc-ArH]
8.5-10.0 ppm [β, α', β', 13.2 H (13H), Por-β, Pc-ArH] theoretical values in parenthesis

Example 4
8(ZnPc-ZnPor)

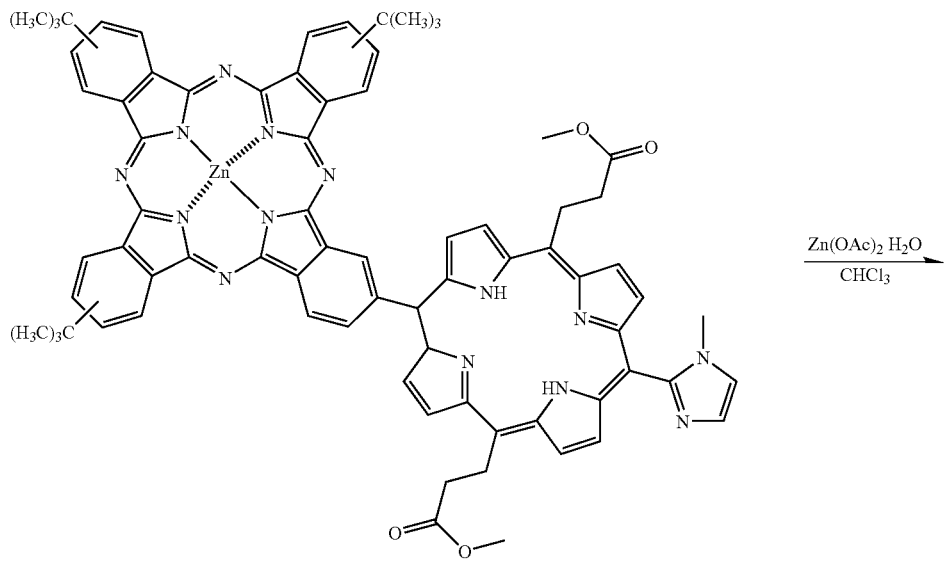

7 (ZnPc-H₂Por)
$C_{76}H_{68}N_{14}O_4Zn$
Exact Mass: 1304.48
Mol. Wt.: 1306.84

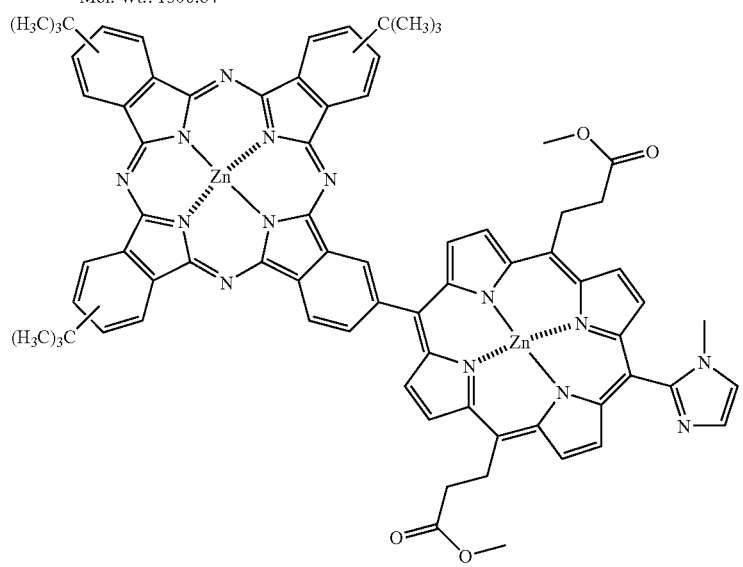

8 (ZnPc-ZnPor)
$C_{76}H_{66}N_{14}O_4Zn_2$
Exact Mass: 1366.40
Mol. Wt.: 1370.21

Tri-tert-butylphthalocyanato Zn(II) porphyrin (8.2 mg/6.3 mmol) was dissolved in CHCl₃ (4.0 mL), 2 to 3 drops of saturated zinc acetate dihydrate solution in MeOH was added to the reaction solution with a Pasteur pipette, and the mixture was stirred at room temperature for 0.5 hour. After confirmation of Zn incorporation by MALDI-TOF MASS spectrum measurement, the reaction solution was poured into distilled water and washed with distilled water. The organic layer was dried over sodium sulfate, and the solvent was evaporated, to give a bright green compound.

Yield: 6.3 mg, 73%

TLC: Rf=0.5, CHCl₃:Py=15:1

UV-vis $\lambda_{max}$/nm (absorbance) CHCl₃: 687.50 (0.6682), 618.00 (0.1418), 569.00 (0.0569), 433.00 (0.4909), 414.50 (0.4305), 349.50 (0.3469)

MALDI-TOFMASS (matrix: dithranol)

m/z: M⁺ 1366.70 (Calc. $C_{76}H_{66}N_{14}O_4Zn_2$: 1366.40), Dimer (2740.25)

27
[Formula 20]
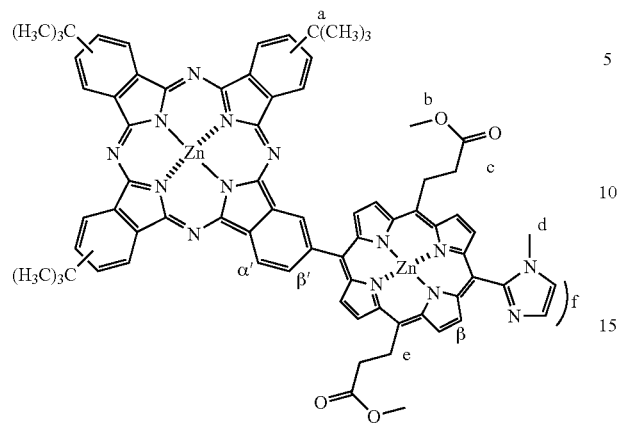
28
$^1$H NMR (Pyridine-$d_5$, 600 MHz)
1.2-1.5 ppm [a 27 H (27 H), tert-butyl]
3.0-3.5 ppm [b, c, d, 13.3 H (13 H), OMe-CH$_2$—, $_{Imi\text{-}Me}$]
5.1-5.4 ppm [e, 2.4 H (4 H), Por-CH$_2$—]
6.9-8.1 ppm [f, α', β', 12 H (12H), Imi, Pc-ArH]
8.8-9.8 ppm [β, α', β', Por-β, Pc-ArH, 10 H (10H)] theoretical values in parenthesis
Examples 5 and 6
Preparation of the Dimer of 6 (H$_2$Pc-ZnPor) and the Dimer of 8 (ZnPc-ZnPor) (Tetramers of the Present Invention) by Means of Complementary Coordination Bonds
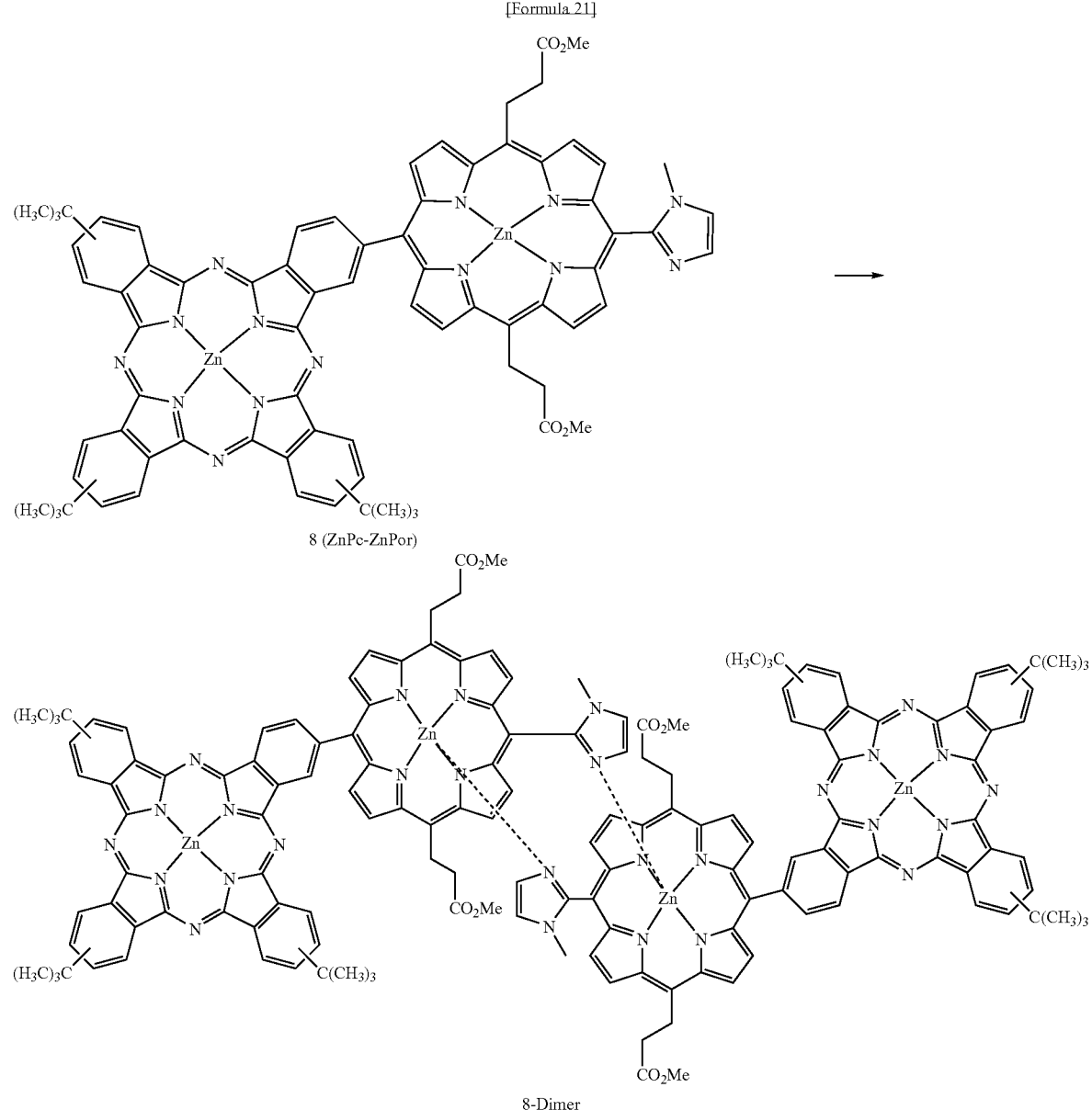

-continued
[Formula 22]

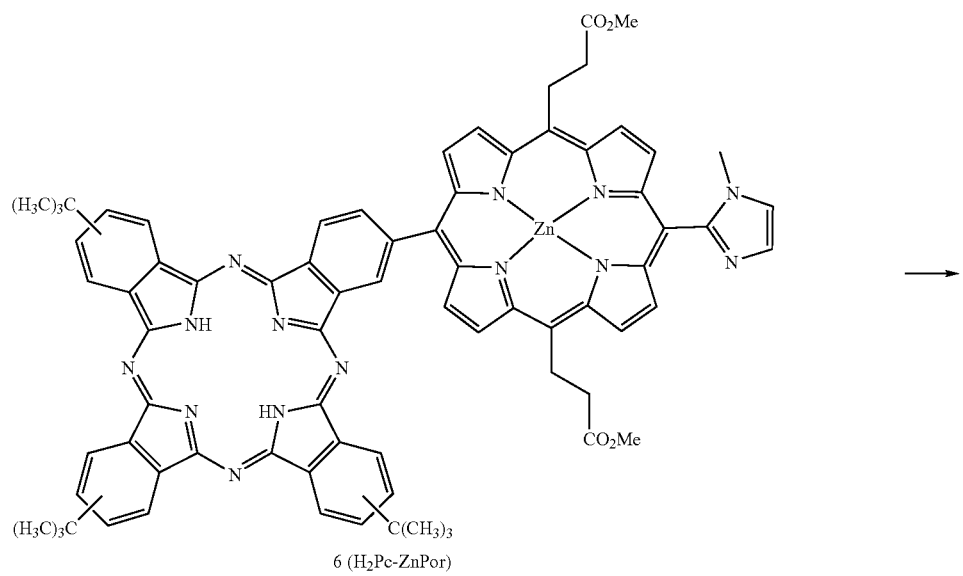

6 (H₂Pc-ZnPor)

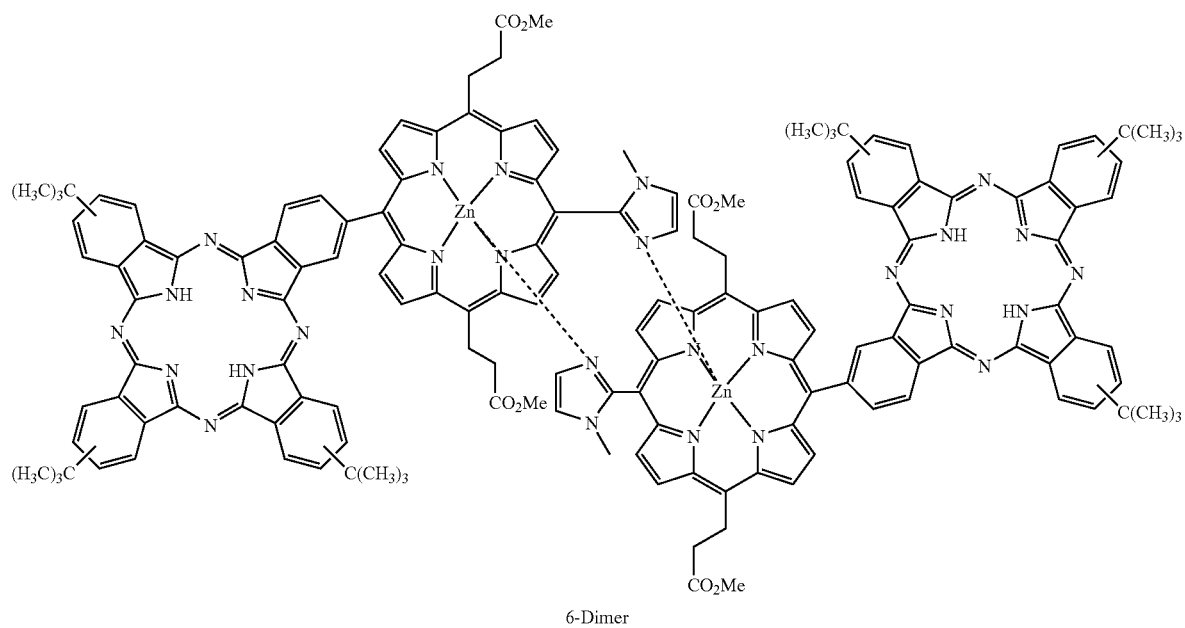

6-Dimer

The meso-connected zinc complex 8, which has an imidazolylporphyrin structure, forms a dimer of 8 (8-dimer) by a complementary self-assembling in a nonpolar solvent, similarly to conventional imidazolylporphyrins. The equilibrium constant of the self-assembling reaction for the imidazolylporphyrin zinc complex is significantly high, for example, as high as $10^{10}$ $M^{-1}$ in chloroform. The absorption spectrum thereof in chloroform is shown in FIG. 1. In FIG. 1, its Soret band is split into two peaks at 413 and 433 nm and has a broad width, which is absorption spectrum characteristic to the self-assemblied dimer of the imidazolylporphyrin zinc complexes. (Reference Document: Kobuke Y.; Miyaji, H., J. Am. Chem. Soc. 1994, 116, 4111-4112). The characteristic peak indicates that the meso-connected zinc complexes 8 forms the dimer of 8 (8-dimer) by self-assembling in chloroform. Similarly, the absorption spectrum of the compound 6 also indicates that the compound 6 forms a dimer structure, which is similar to that of the 8-dimer, in chloroform.

Measurement Example 1

High-Efficiency Energy and Electron Transfer from Porphyrin to Phthalocyanine (i) Comparison between Compound 6 (H₂Pc-ZnPor) and Reference Compound 10

[Formula 23]

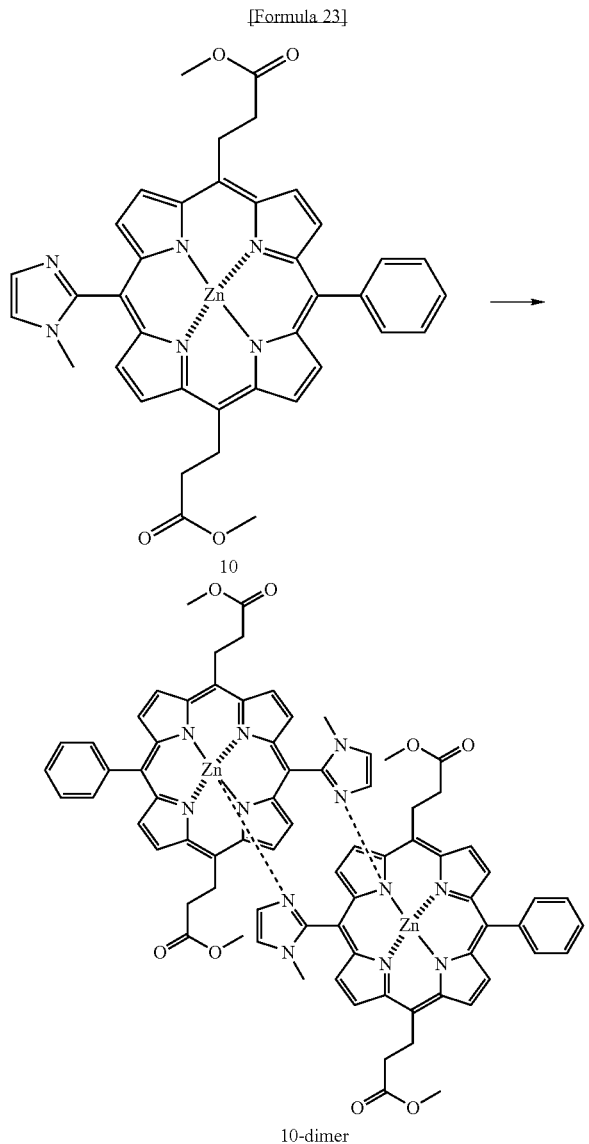

10-dimer (Measurement Method)

Figure 2:
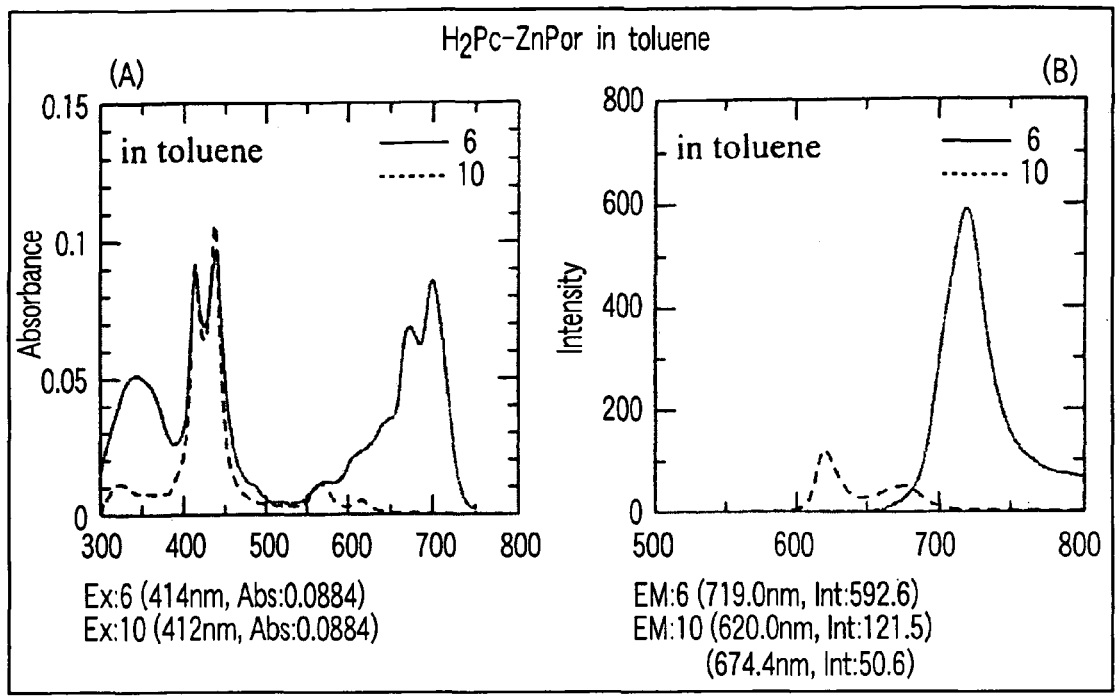
FIG. 2(a) shows the absorption spectra of 6-dimer and 10-dimer in toluene.
FIG. 2(b) shows the fluorescence spectra of 6-dimer and 10-dimer in toluene, as determined at excitation wavelengths of 414 and 412 nm, respectively.
Figure 3:
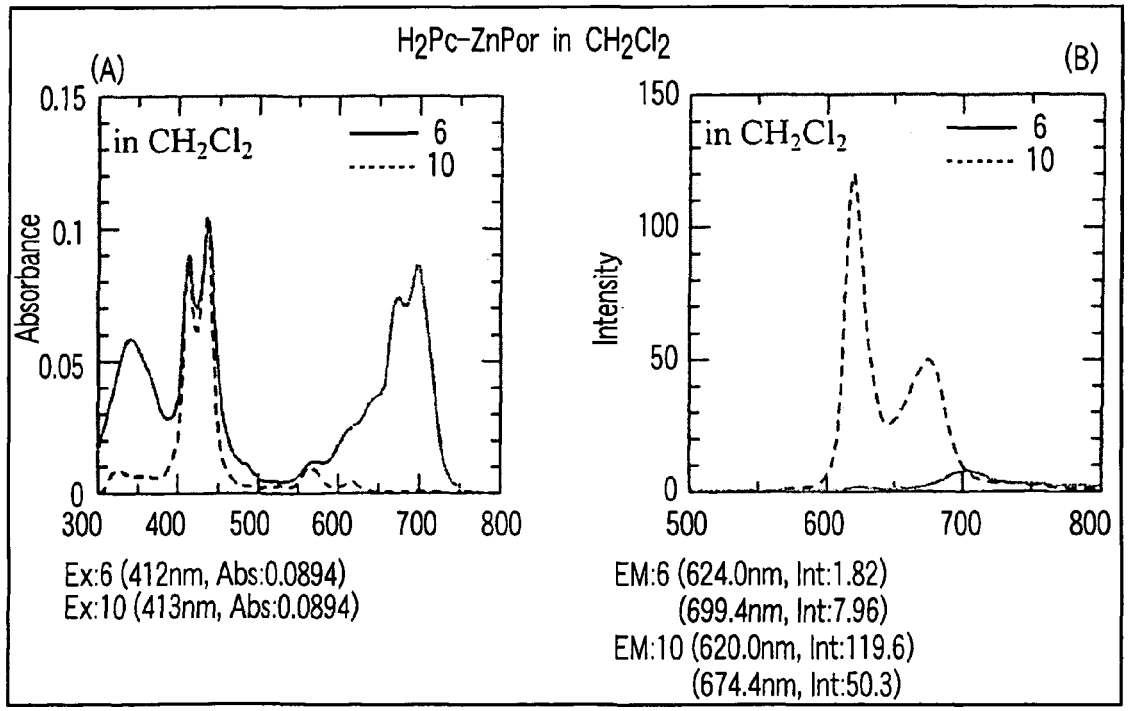
FIG. 3(a) shows the absorption spectra of 6-dimer and 10-dimer in methylene chloride ($CH_2Cl_2$)
FIG. 3(b) shows the fluorescence spectra of 6-dimer and 10-dimer in methylene chloride, as determined at excitation wavelengths of 412 and 413 nm, respectively.

For evaluation of the energy and electron transfer characteristics of the compound 6-dimer, a compound 10-dimer having no phthalocyanine moiety was prepared as a reference compound, and the fluorescence spectra thereof were determined in toluene and methylene chloride for comparison. The absorption and fluorescence spectra of these compounds in respective solvents were shown in FIGS. 2 and 3. The fluorescence spectrum was determined by excitation with a light at around 414 nm, which porphyrin does not absorb. The concentration of the reference compound was so adjusted that the absorbance at the same wavelength becomes the same as that of the compound 6-dimer.

(Result)

As for the 6-dimer in toluene, there is almost no emission from porphyrin and there is emission only from phthalocyanine, which indicates efficient energy transfer from porphyrin to phthalocyanine. On the other hand, as for the 6-dimer in methylene chloride, there is almost no emission both from porphyrin and phthalocyanine, which indicates efficient photoexcited electron transfer from porphyrin to phthalocyanine. Further, when the measurement was performed in chloroform, which had an intermediate dielectric constant between toluene and methylene chloride, there was a medium degree of emission from phthalocyanine. The result suggests that energy transfer occurs from some part of the excited porphyrin species to phthalocyanine and electron transfer occurs from the other part thereof to phthalocyanine. These results showed that the 6-dimer caused energy transfer and electron transfer competitively, depending on the dielectric constant of the solvent.

Measurement Examples 2 to 4

The high-efficiency energy and electron transfer from porphyrin to phthalocyanine of the other compounds 5, 7, and 8 was determined in a method similar to the Measurement Example 1, and these compounds also showed a "solvent-fluorescence intensity relationship" similar to that in Measurement Example 1.

Measurement Example 5

Measurement of two-photon-absorption cross section

The two-photon-absorption cross section was determined by open Z-scanning technique (see the reference documents below). The solvent used was toluene; the sample concentration of the dimer of 8 (ZnPc-ZnPor) (porphyrin/phthalocyanine tetramer of the present invention) was 0.47 mM; and that of the reference compound zinc tetra-t-butylphthalocyanine (Zn-tetra-t-bu-Pc) was 18 mM. A 1-mm cell was used for measurement. The area within 40 mm from the focal point (lens focal length: 100 mm) was scanned by using a Q-switch Nd:YAG pulsed laser having a pulse width of 5 nanoseconds (incident beam: 35 mW or less, repetition: 10 Hz). The measurement interval was 1 mm. The wavelength was changed in the range from 780 nm to 1,300 nm by using an optical parametric oscillator (OPO). The two-photon-absorption cross section $\sigma^{(2)}$ was determined according to the following Formula:

$$\sigma^{(2)} = h\nu\beta/N \quad (1)$$

where hv represents a photon energy; N represents a molecular number density; and $\sigma^{(2)}$ represents a two-photon absorption coefficient, which is expressed by the following relationship.

$$q = \beta I_0 L \quad (2)$$

where the parameter q represents a two-photon absorbance, which is obtained by fitting the obtained open Z-scanning curve with Gaussian Formula; and $I_0$ represents the intensity of incident light (see the following documents for measurement and analytical methods).

(IEEE. J. Quant. Electron. 26, 760, (1990), and Handbook of Nonlinear Optics, Marcel Dekker, New York (1996))

Figure 4:
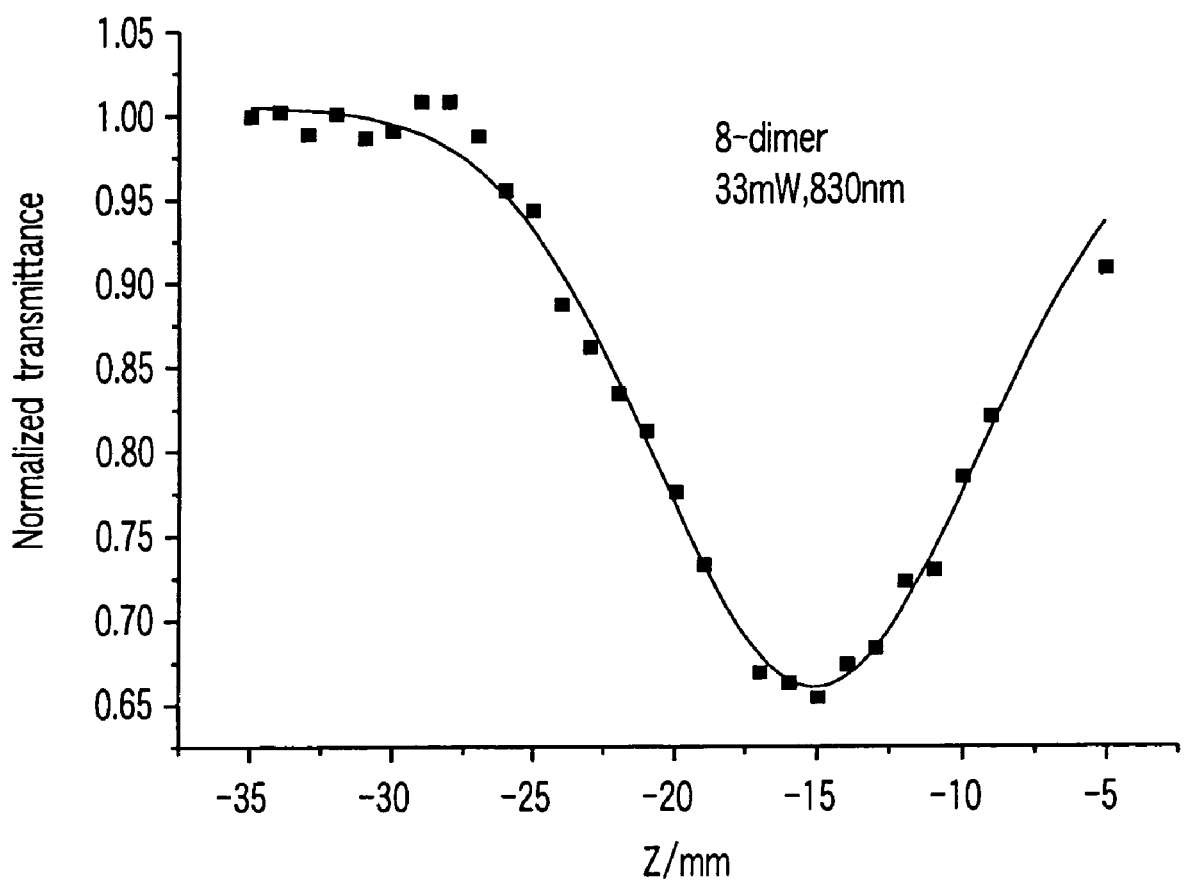
FIG. 4 is a graph showing an observed Z-scanning curve of the dimer of the dimer 8 (ZnPc-ZnPor) of the present invention (porphyrin/phthalocyanine tetramer of the present invention). The points in the graph are observed values, and the solid line is a curve obtained by fitting with Gaussian Formula. The laser power is 33 mW, and the wavelength is 830 nm.

Typical Z-scan curve of the dimer of 8 (ZnPc-ZnPor), as determined according to the method above, is shown in FIG. 4. The points in the figure are observed values, and the solid line is a curve obtained by fitting with Gaussian Formula. The laser power was 33 mW, and the wavelength was 830 nm.

The two-photon absorption spectrum of the dimer of 8 (ZnPc-ZnPor), as determined by the method above, is shown in FIG. 5. The figure inserted in FIG. 5 shows the two-photon absorption spectrum of the reference compound Zn-tetra-t-bu-Pc as determined similarly.

The two-photon-absorption cross section $\sigma^{(2)}$ is plotted on the vertical axis of spectrum, and the unit GM is equivalent to $1\times10^{-50}$ cm$^4$ s photon$^{-1}$. The maximum two-photon-absorption cross section in the dimer of 8 was 36,800 GM (820 nm), which was approximately 128 times greater than that of Zn-tetra-t-bu-Pc of 288 GM (840 nm). It seems that direct connection between phthalocyanine and porphyrin leads to increase in polarization of the entire molecule and to increase in the transition probability of two-photon absorption.

INDUSTRIAL APPLICABILITY

The dimer represented by Formula (A-1) and the tetramer represented by Formula (A-2) of the present invention are expected to be applicable to photoelectric conversion elements (see Non-patent Document 10 and Patent Document 2) and three-dimensional nonlinear optical materials (see Non-patent Document 11 and Patent Document 3). More specifically, the dimer represented by Formula (A-1) and the tetramer represented by Formula (A-2) of the present invention are available as a polymer terminal molecule, as described in Patent Document 4 (Jpn. Pat. Appln. KOKAI Publication No. 2004-266100) and Patent Document 5 (Jpn. Pat. Appln. KOKAI Publication No. 2004-137273). As described in the Measurement Example 1, the dimer and tetramer of the present invention is also available as a fluorescence probe, by using the phenomenon of the phthalocyanine emission by excitation of porphyrin; and the efficiency thereof is higher than that of the compound described in Non-patent Document 6. In addition, the dimer and tetramer of the present invention are also useful in preparation of a photoelectric converting material, because they can cause electron transfer by introducing them into the terminal of a porphyrin multimer by using the method described in Patent Document 4 (Jpn. Pat. Appln. KOKAI Publication No. 2004-266100). Further, the dimer and tetramer of the present invention are materials larger in two-photon-absorption cross section, as described in the Measurement Example 5, and thus, are usable as a two-photon-absorbing material (one of nonlinear optical properties), which is applicable, for example, to photodynamic therapy of tumors and as three dimensional memory, optical switch, and the like.

What is claimed is:

1. A compound represented by the following Formula (A-2):

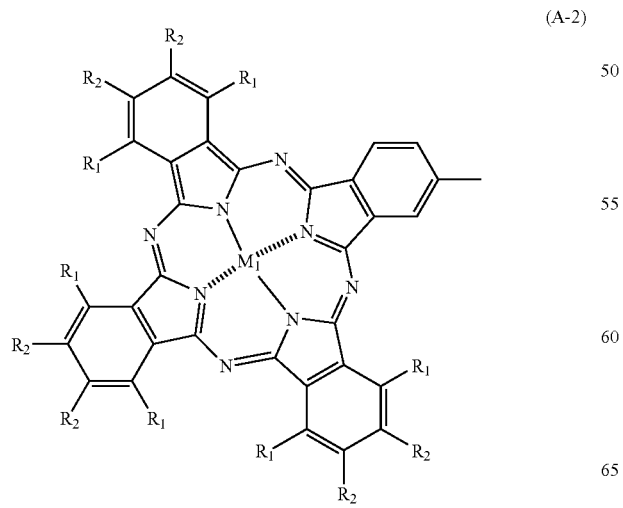

(A-2)

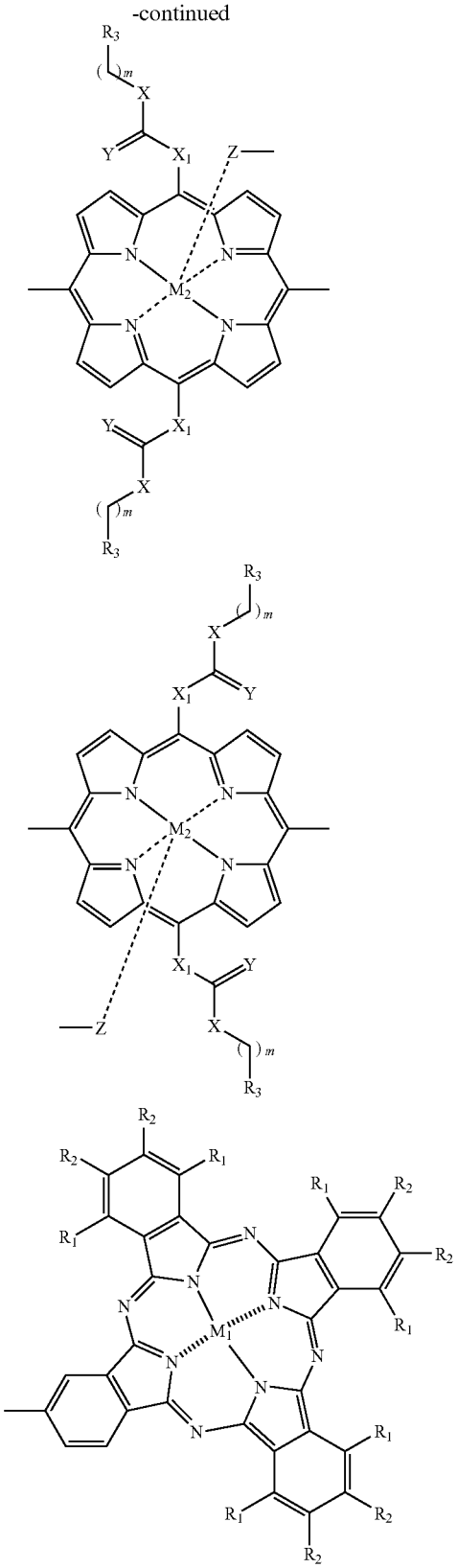

where $R_1$, $R_2$, and $R_3$ may be the same or different, and each represents a hydrogen atom or an alkyl or alkyloxy group;

$M_1$ and $M_2$, may be the same or different, $M_1$ represents two protons or a first bivalent or trivalent metal ion, $M_2$ represents a second bivalent or trivalent metal ion, and each of the first bivalent or trivalent metal ion and the second bivalent or trivalent metal ion is formed from an atom of an element selected from the group consisting of Mg, Zn, Cd, Hg, Al, Ga, In, Tl, Si, Ge, Sn, Pb, P, As, Sb, Bi, Sc, Y, La, Ce, Pr, Nd, Pm, Sm, Eu, Gd, Tb, Dy, Ho, Er, Tm, Yb, Lu, Ti, Zr, Hf, V, Nb, Ta, Cr, Mo, W, Mn, Tc, Re, Fe, Ru, Os Co, Rh, Ir, Ni, Pd, Pt, Cu, Ag, and Au;

$X_1$ represents a single bond or an alkylene group;

X represents —O—, —S—, >$NR_{101}$(where $R_{101}$ represents H or alkyl group), $CH_2$, or a single bond;

Y represents 2H, =O or =S;

m is an integer of 0 to 4; and

Z represents a five- or six-membered nitrogen-containing coordinating heteroaromatic ring group, the alkyl or alkyloxy group comprises a tertiary alkyl group.

5. The compound according to claim 1, wherein $X_1$ represents the alkylene group; and the carbon number of the alkylene group is 1 to 6.

6. The compound according to claim 1, wherein X represents —O—.

7. The compound according to claim 1, wherein Y represents =O.

8. The compound according to claim 1, wherein m is 1.

9. The compound according to claim 1, wherein the five- or six-membered nitrogen-containing coordinating heteroaromatic ring group represented by Z is an alkyl-substituted or unsubstituted imidazolyl group.

10. A method of producing the compound represented by the following Formula (A-2)

[Formula 25]

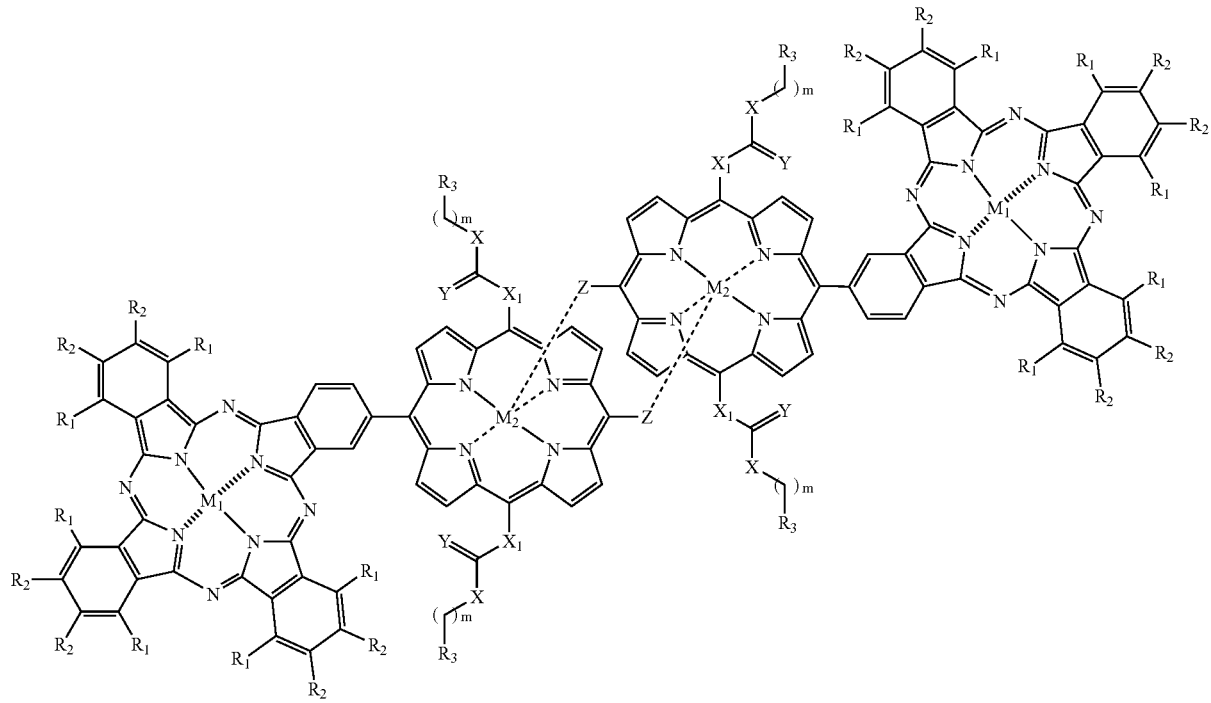

(A-2)

provided that multiple substituent groups represented by the same character may be the same or different.

2. The compound according to claim 1, wherein the carbon number of the alkyl group or alkyloxy group represented by $R_1$, $R_2$, or $R_3$ is 1 to 20; the carbon number of the alkylene group represented by $X_1$ is 1 to 6; and the five- or six-membered nitrogen-containing coordinating heteroaromatic ring group represented by Z is an alkyl-substituted or unsubstituted imidazolyl, oxazolyl, thiazolyl or pyridyl group.

3. The compound according to claim 1, wherein at least one of $R_1$, $R_2$, and $R_3$ represents the alkyl or alkyloxy group; and the carbon number of the alkyl or alkyloxy group is 1 to 20.

4. The compound according to claim 1, wherein at least one of $R_1$, $R_2$, and $R_3$ represents the alkyl or alkyloxy group; and where $R_1$, $R_2$, and $R_3$ may be the same or different, and each represents a hydrogen atom or an alkyl or alkyloxy group;

$M_1$ and $M_2$ may be the same or different, $M_1$ represents two protons or a first bivalent or trivalent metal ion, $M_2$ represents a second bivalent or trivalent metal ion, and each of the first bivalent or trivalent metal ion and the second bivalent or trivalent metal ion is formed from an atom of an element selected from the group consisting of Mg, Zn, Cd, Hg, Al, Ga, In, Tl, Si, Ge, Sn, Pb, P, As, Sb, Bi, Sc, Y, La, Ce, Pr, Nd, Pm, Sm, Eu, Gd, Tb, Dy, Ho, Er, Tm, Yb, Lu, Ti, Zr, Hf, V, Nb, Ta, Cr, Mo, W, Mn, Tc, Re, Fe, Ru, Os, Co, Rh, Ir, Ni, Pd, Pt, Cu, Ag, and Au;

$X_1$ represents a single bond or an alkylene group;

X represents —O—, —S—, >NR$_{101}$(where R$_{101}$ represents H or alkyl group), CH$_2$, or a single bond;

Y represents 2H, =O or =S;

m is an integer of 0 to 4; and

Z represents a five- or six-membered nitrogen-containing coordinating heteroaromatic ring group, provided that multiple substituent groups represented by the same character may be the same or different, the method comprising the steps of (a) reacting a phthalocyanine aldehyde represented by the following Formula (A-5)

[Formula 26]

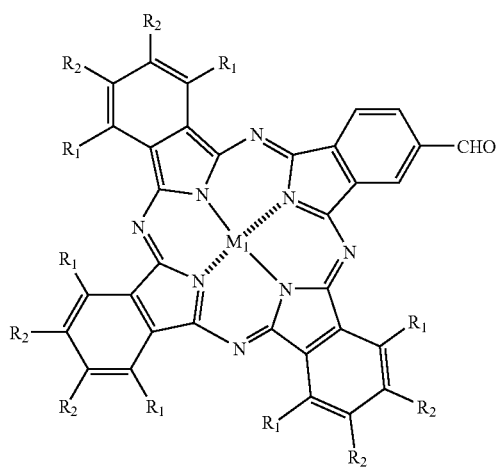

(A-5)

where respective substituent groups are the same as those defined in the above-mentioned Formula (A-2) with a dipyrrole compound represented by the following Formula (A-6)

[Formula 27]

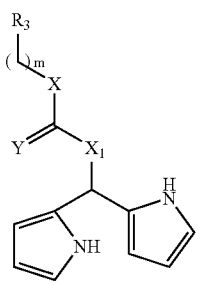

(A-6)

where respective substituent groups are the same as those defined in the above-mentioned Formula (A-2) in the presence of an organic solvent;

(b) reacting the product of the step (a) with an aldehyde represented by Z—CHO (Z is the same as that defined in the above-mentioned Formula (A-2);

(c) introducing M$_2$ as the porphyrin-ring central metal into the product of the step (b) to obtain the compound represented by the following Formula (A-1)

[Formula 24]

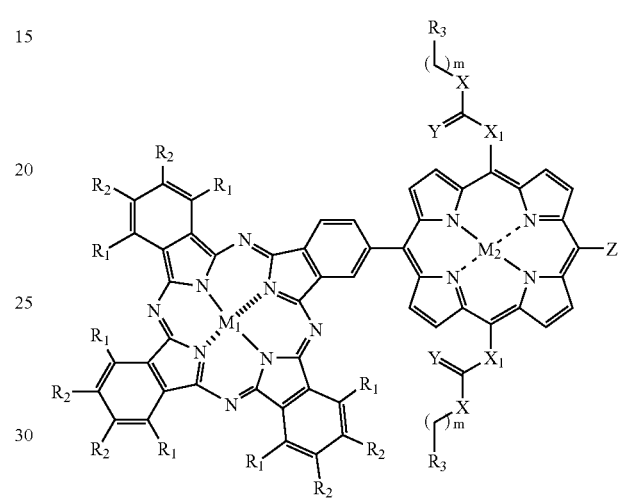

(A-1)

where respective substituent groups are the same as those defined in the above-mentioned Formula (A-2), and (d) self-assembling the compound represented by the Formula (A-1) in a solvent selected from the group consisting of chloroform, benzene and toluene.

11. The method according to claim 10, wherein at least one of R$_1$, R$_2$, and R$_3$ represents the alkyl or alkyloxy group; and the carbon number of the alkyl or alkyloxy group is 1 to 20.

12. The method according to claim 10, wherein X$_1$ represents the alkylene group; and the carbon number of the alkylene group is 1 to 6.

13. The method according to claim 10, wherein X represents —O—.

14. The method according to claim 10, wherein Y represents =O.

15. The method according to claim 10, wherein m is 1.

16. The compound according to claim 10, wherein the five- or six-membered nitrogen-containing coordinating heteroaromatic ring group represented by Z is an alkyl-substituted or unsubstituted imidazolyl group.

* * * * *